United States Patent [19]
Demuth, Jr. et al.

[11] Patent Number: 5,530,116
[45] Date of Patent: Jun. 25, 1996

[54] ANTIMICROBIAL QUINOLONYL LACTAMS

[75] Inventors: Thomas P. Demuth, Jr., Norwich; Ronald E. White, South Plymouth, both of N.Y.

[73] Assignee: The Procter & Gamble Company, Cincinnati, Ohio

[21] Appl. No.: 361,919

[22] Filed: Dec. 22, 1994

Related U.S. Application Data

[63] Continuation of Ser. No. 511,483, Apr. 18, 1990, abandoned.

[51] Int. Cl.$^6$ .................................................. C07D 501/57
[52] U.S. Cl. .......................... 540/221; 540/222; 540/225; 540/227
[58] Field of Search .................................. 540/222, 215, 540/221, 227

[56]                  References Cited

U.S. PATENT DOCUMENTS

| | | | |
|---|---|---|---|
| 4,146,719 | 3/1979 | Irikura | 544/363 |
| 4,620,007 | 10/1986 | Grohe et al. | 546/156 |
| 4,631,150 | 12/1986 | Battistini et al. | 540/310 |
| 4,670,444 | 6/1987 | Grohe et al. | 514/300 |
| 4,742,053 | 5/1988 | Nakagawa et al. | 514/202 |
| 4,904,647 | 2/1990 | Kulcsar et al. | 514/154 |
| 5,013,730 | 5/1991 | Arnould et al. | 514/202 |
| 5,013,731 | 5/1991 | Arnould et al. | 514/202 |
| 5,147,871 | 9/1992 | Allnecht et al. | 514/202 |
| 5,159,077 | 10/1992 | Keith et al. | 540/222 |
| 5,162,523 | 11/1992 | Keith et al. | 540/227 |
| 5,189,157 | 2/1993 | Wei et al. | 540/222 |

FOREIGN PATENT DOCUMENTS

| | | |
|---|---|---|
| 75009/87 | 1/1988 | Australia . |
| 8775009 | 1/1988 | Australia . |
| 8827554 | 6/1989 | Australia . |
| 53816 | 6/1982 | European Pat. Off. . |
| 62328 | 10/1982 | European Pat. Off. . |
| 203559 | 12/1986 | European Pat. Off. . |
| 0304158 | 2/1989 | European Pat. Off. . |
| 335297 | 10/1989 | European Pat. Off. . |
| 341990 | 11/1989 | European Pat. Off. . |
| 0366640 | 5/1990 | European Pat. Off. . |
| 0366193 | 5/1990 | European Pat. Off. . |
| 0366643 | 5/1990 | European Pat. Off. . |
| 0366189 | 5/1990 | European Pat. Off. . |
| 0366641 | 5/1990 | European Pat. Off. . |
| 0453952 | 10/1991 | European Pat. Off. . |
| 0453924 | 10/1991 | European Pat. Off. . |
| 0451764 | 10/1991 | European Pat. Off. . |
| 2191556 | 3/1974 | France . |
| 2243940 | 4/1975 | France . |
| 1940511 | 3/1970 | Germany . |
| 2322750 | 11/1972 | Germany . |
| 2448966 | 4/1975 | Germany . |
| 2514322 | 10/1975 | Germany . |
| 2947948 | 6/1980 | Germany . |
| 3345093 | 6/1984 | Germany . |
| 47-11237 | 4/1972 | Japan . |
| 49-35392 | 4/1974 | Japan . |
| 50-23037 | 8/1975 | Japan . |
| 50-23036 | 8/1975 | Japan . |
| 57-32290 | 2/1982 | Japan . |
| 57-46988 | 3/1982 | Japan . |
| 57-46990 | 3/1982 | Japan . |
| 60-06617 | 1/1985 | Japan . |
| 1258684 | 10/1989 | Japan . |
| 8705297 | 9/1987 | WIPO . |
| 9116310 | 10/1991 | WIPO . |

OTHER PUBLICATIONS

Uglesic et al., "New Semisynthetic Penicillins", *Advan. Antimicrob. Antineoplastic Chemother., Proc. Int. Congr. Chemother.*, 7th, Meeting Date 1971, vol. 1, 997 (1972) (*Chemical Abstracts* 79:61968).

O'Callaghan, et al., "A New Cephalosporin with a Dual Mode of Action", 10 *Antimicrobial Agents and Chemotherapy* 245 (1976).

(List continued on next page.)

*Primary Examiner*—Nicholas Rizzo
*Attorney, Agent, or Firm*—Richard A. Hake; William J. Winter; David L. Suter

[57]                        ABSTRACT

Antimicrobial quinolonyl lactam compounds comprising a lactam-containing moiety linked to a quinolone moiety, of the formula:

$$\begin{array}{c} \text{O} \quad\quad \text{O} \quad\quad R^6 \\ \| \quad\quad \| \\ R^4\text{—C} \\ \quad\quad A^3 \diagdown_{N'} \diagup A^1 \diagdown R^3 \\ \quad\quad\quad\quad | \\ \quad\quad\quad\quad R^1 \end{array}$$

wherein (1) $A^1, A^2, A^3, R^1$, and $R^4$ generally form any of a variety of quinolone, naphthyridine or related cyclic moieties known in the art to have antimicrobial activity; and (2) $R^6$ is part of a linking moiety, linking the quinolone moiety to a lactam-containing moiety having the formula:

$$R^{10}\text{—}\overset{R^{11}}{\underset{\|}{\text{C}}}\text{—}\overset{R^{12}}{\underset{}{\text{C}}}\diagdown_a\diagup R^{14}\text{—L}$$
$$\underset{\text{O}}{\|}\quad\quad\text{N''}R^{13}\diagup^b$$

wherein (3) $R^{10}, R^{11}, R^{12}, R^{13}$, and $R^{14}$, together with bonds "a" and "b", form any of a variety of lactam-containing moieties known in the art to have antimicrobial activity; and (4) the linking moiety includes (for example) carbamate, dithiocarbamate, urea, thiourea, isouronium, isothiouronium, guanidine, carbonate, trithiocarbonate, reversed carbamate, xanthate, reversed isouronium, reversed dithiocarbamate, reversed isothiouronium, amine, imine, ammonium, heteroarylium, ether, thioether, ester, thioester, amide, and hydrazide groups.

30 Claims, No Drawings

OTHER PUBLICATIONS

Greenwood et al., "Dual–Action Cephalosporin Utilizing a Novel Therapeutic Principle", 10 *Antimicrobial Agents and Chemotherapy* 249 (1976).

Yamada et al., "New Broad–Spectrum Cephalosporins with Antipseudomonal Activity", 36 *J. Antibiotics* 532 (1983) (*Chemical Abstracts* 99:87869).

Hirose et al., "Desulfurization of 7–Aminodeacetoxycephalosporanic Acid", 104 *Yakugaku Zasshi* 302 (1984) (*Chemical Abstract* 101:110596).

Cimarusti et al., "Monocyclic β–Lactam Antibiotics", 4 *Medicinal Research Reviews* 1 (1984).

Dürckheimer et al., "Recent Developments in the Field of β–Lactam Antibiotics", 24 *Angew. Chem. Int. Ed. Engl.* 180 (1985).

Wolfson et al., "Minireview–The Fluoroquinolones: Structures, Mechanisms of Action and Resistance, and Spectra of Activity In Vitro", 28 *Antimicrobial Agents and Chemotherapy* 581 (1985).

Mobashery et al., "Conscripting β–Lactamase for use in Drug Delivery. Synthesis and Biological Activity of a Cephalosporin $C_{10}$–Ester of an Antibiotic Dipeptide", 108 *J. American Chemical Society* 1685 (1986).

Mobashery et al., "Reactions of *Escherichia coli* TEM β–Lactamase with Cephalothin and with $C_{10}$–Dipeptidyl Cephalosporin Esters", 261 *J. Biological Chemistry* 7879 (1986).

Rolinson, "β–Lactam antibiotics", 17 *J. Antimicrobial Chemotherapy* 5 (1986).

Wise, "Minireview–In Vitro and Pharmacokinetic Properties of the Carbapenems", 30 *Antimicrobial Agents and Chemotherapy* 343 (1986).

Mobashery et al., "Inactivation of Alanine Racemase by β–Chloro–L–alanine Released Enzymatically from Amino Acid and Peptide $C_{10}$ Esters of Deacetylcephalothin", 26 *Biochemistry* 5878 (1987).

Thabaut et al., "Beta–lactam Antibiotic–New Quinolone Combinations", 16 *Presse Med.* 2167 (1987) (*Chemical Abstracts* 108:147028).

Le Noc et al., "Active Antibacterienne in vitro du Cefpirome en Association Avec Quatre Aminoglycosides et Deux Fluoroquinolones", 36 *Path. Biol.* 762 (1988).

McCombie et al., "Synthesis and In Vitro Activity of the Penem Antibiotics", 8 *Medicinal Research Reviews* 393 (1988).

Albrecht et al., "Dual–Action Cephalosporins: An Idea Whose Time Has Come", *Program and Abstracts of the Twenty–Eighth Interscience Conference on Antimicrobial Agents and Chemotherapy* 186 (American Society for Microbiology, 1988).

Georgopapadakou et al., "Cephalosporin–Quinolone Esters: Biological Properties", *Program and Abstracts of the Twenty–Eighth Interscience Conference on Antimicrobial Agents and Chemotherapy* 186 (American Society for Microbiology, 1988).

Christenson et al., "Hydrolysis of Ro 23–9424 by β–Lactamases", *Program and Abstracts of the Twenty–Eighth Interscience Conference on Antimicrobial Agents and Chemotherapy* 187 (American Society for Microbiology, 1988).

Christenson et al., "Mode of Action of Ro 23–9424, a Dual–Action Cephalosporin", *Program and Abstracts of the Twenty–Eighth Interscience Conference on Antimicrobial Agents and Chemotherapy* 187 (American Society for Microbiology, 1988).

Georgopapadakou et al., "Mode of Action of the Dual–Action Cephalosporin Ro 23–9424", *Program and Abstracts of the Twenty–Eighth Interscience Conference on Antimicrobial Agents and Chemotherapy* 187 (American Society for Microbiology, 1988).

Jones et al., "Antimicrobial Activity of Ro 23–9424, a Novel Ester Fusion of Fleroxacin and Desacetyl–Cefotaxime", *Program and Abstracts of the Twenty–Eighth Interscience Conference on Antimicrobial Agents and Chemotherapy* 187 (American Society for Microbiology, 1988).

Beskid et al., "In Vitro Antibacterial Activity of Dual–Action Cephalosporin Ro 23–9424 Compared to Cefotaxime and Fleroxacin", *Program and Abstracts of the Twenty–Eighth Interscience Conference on Antimicrobial Agents and Chemotherapy* 187 (American Society for Microbiology, 1988).

Christenson et al., "Pharmacokinetics of Ro 23–9424, a Dual–Action Cephalosporin in Animals", *Program and Abstracts of the Twenty–Eighth Interscience Conference on Antmicrobial Agents and Chemotherapy* 188 (American Society for Microbiology, 1988).

Christenson et al., "Mode of Action of Ro 23–5068, a Dual–Action Cephalosporin", *Program and Abstracts of the Twenty–Eighth Intersciencen Conference on Antimicrobial Agents and Chemotherapy* 188 (American Society for Microbiology, 1988).

Albrecht et al., "Dual–Action Cephalosporins: An Idea Whose Time Has Come", Poster Session: 28th Interscience Conference on Antimicrobial Agents and Chemotherapy (Oct. 24, 1988).

Georgopapadakou et al., "Cephalosporin–Quinolone Esters: Biological Properties", Poster Session: 28th Interscience Conference on Antimicrobial Agents and Chemotherapy (Oct. 24, 1988).

Christenson et al., "Hydrolysis of Ro 23–9424 by β–Lactamases", Poster Session: 28th Interscience Conference on Antimicrobial Agents and Chemotherapy (Oct. 24, 1988).

Christenson et al., "Mode of Actioin of Ro 23–9424, a 'Dual–Action' Cephalosporin", Poster Session: 28th Interscience conference on Antimicrobial Agents and Chemotherapy (Oct. 24, 1988).

Georgopapadakou et al., "Mode of Action of the Dual–Action Cephalosporin Ro 23–9424", Poster Session: 28th Interscience Conference on Antimicrobial Agents and Chemotherapy (Oct. 24, 1988).

Beskid et al., "In Vitro Antibacterial Activity of Dual–Action Cephalosporin Ro 23–9424 and Comparative Agents", Poster Session: 28th Interscience Conference on Antimicrobial Agents and Chemotherapy (Oct. 24, 1988).

Beskid et al., "In Vivo Antibacterial Activity of Dual–Action Cephalosporin Ro 23–9424 Compared to Cefotaxime and Fleroxacin", Poster Session: 28th Interscience Conference on Antimicrobial Agents and Chemotherapy (Oct. 24, 1988).

Christenson et al., "Pharmacokinetics of Ro 23–9424, a Dual–Action Cephalosporin, in Animals", Poster Session: 28th Interscience Conference on Antimicrobial Agents and Chemotherapy (Oct. 24, 1988).

Christenson et al., "Mode of Action of Ro 23–5068, a Dual–Action Cephalosporin", Poster Session: 28th Interscience Conference on Antimicrobial Agents and Chemotherapy (Oct. 24, 1988).

Georgopapadakou et al., "Mode of Action of the Dual–Action Cephalosporin Ro 23–9424", 33 *Antimicrobial Agents and Chemotherapy* 1067 (1989).

Cleeland et al., "Dual–Action Antibacterials: A Concept Newly Recognized for Antibacterial Chemotherapy", 6 Antimicrobic Newsletter 61 (1989).

Albrecht et al., "Dual–Action Cephalosporins: Cephalosporin-3'-Quaternary Quinolones", *Program and Abstracts of the Twenty–Ninth Interscience Conference on Antimicrobial Agents and Chemotherapy* (American Society for Microbiology, 1989).

Perrone, E. et al., "Dual Action Penems", Abstract #825: *Abstract of the 1991 ICAAC* (Abstract only).

albrecht, H. A., "Dual–Action Cephalosporins Incorporating 3'-Tertiary Amine–Linked Quinolones", 31st *Interscience Conference on Antibacterial Agents and Chemotherapy*, Chicago, Illinois; Poster Session: Oct. 2, 1991 (Abs. & Poster).

Corraz, A. J. et al., "Dual–Action Penems and Carbapenems", Abstract #826, Poster #73, *31st Interscience Conference on Antimicrobial Agents and Chemotherapy* (Chicago, Illinois), Oct. 1, 1991 (Abstract & Poster).

Schaefer, F. f. et al., "The Role of AMPC β–Lactamase in the Mechanism of Action of Ester–Linked Dual–Action Cephalosporins", Abstract #953, *31st Interscience Conference on Antimocribial Agents and Chemotherapy,* Poster Session, Oct. 1, 1991 (Abstract & Poster).

Bartkovitz, D., et al., "The Synthesis and Biological Properties of 2a–Methyl Substituted Penicillins", Abstract #824, 31st Interscience Conference on Antibacterial Agents and Chemotherapy (Chicago, Illinois), Oct. 1, 1991 (Abstract & Poster).

Demuth, T. P., et al., "Synthesis and Antibacterial Activity of New C–10 Quinolonyl–Cephem Esters", *The Journal of Antibiotics,* vol. 44, No. 2, pp. 200–209, Feb. 1991.

ANTIMICROBIAL QUINOLONYL LACTAMS

This is a continuation of application Ser. No. 07/511,483, filed on Apr. 18, 1990, now abandoned.

BACKGROUND OF THE INVENTION

This invention relates to novel antimicrobial compounds and compositions. The compounds of this invention contain, as integral substituents, a quinolone moiety and a lactam-containing moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The development of microbial resistance is one factor in the selection of an appropriate antimicrobial (particularly antibacterials), which is of increasing concern in medical science. This "resistance" can be defined as existence of organisms, within a population of a given microbial species, that are less susceptible to the action of a given antimicrobial agent. Such resistant strains may subvert the mechanism of action of a particular antimicrobial, or chemically degrade the antimicrobial before it can act. For example, bacterial resistance to beta-lactam antibacterials has arisen through development of bacterial strains that produce beta-lactamase enzymes, which degrade the antibacterial.

In part as a result of the intense use of antibacterials over extended periods of time, many highly resistant strains of bacteria have evolved. This is of particular concern in environments such as hospitals and nursing homes, which are characterized by relatively high rates of infection and intense use of antibacterials. See, e.g., W. Sanders, Jr. et al., "Inductible Beta-lactamases: Clinical and Epidemiologic Implications for Use of Newer Cephalosporins", 10 *Reviews of Infectious Diseases* 830 (1988). Indeed, the development of resistant bacterial strains has led to a concern that pathogenic bacteria may be produced that are essentially resistant to even the newest developed antibacterial agents.

The literature describes many attempts to enhance the efficacy of antimicrobials, and to overcome the development of microbial resistance. Many such attempts involve the combination of antimicrobials. For example, Thabaut et al., 16 *Presse Med.* 2167 (1987) describes combinations of pefloxacin (a quinolone) with the beta-lactams cefotaxime and cefsulodin. Lenoc et al., 36 *Path. Biol.* 762 (1988), describes combined use of cephems with aminoglycosides, and with quinolones. Japanese Patent Publication 60/06,617, published Jan. 14, 1985, also describes compositions containing beta-lactams and quinolones. O'Callaghan et al., 10 *Antimicrobial Agents and Chemotherapy* 245 (1976), describes a mercapto pyridine-substituted cephem, which is said to liberate an active antimicrobial agent when the cephalosporin is hydrolyzed by beta-lactamase. Mobashery et al., 108 *J. American Chemical Society* 1684 (1986), presents a theory of employing bacterial beta-lactamase in situ to release an antibacterially-active leaving group from the 10-position of a cephem.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology.

SUMMARY OF THE INVENTION

The present invention provides compounds of the general structure

wherein Q, L and B are defined as follows:
(I) Q is a structure according to Formula (I)

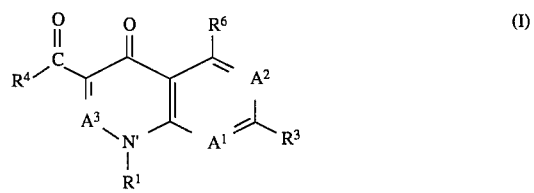

wherein
(A) (1) $A^1$ is N or $C(R^7)$; where
  (i) $R^7$ is hydrogen, hydroxy, alkoxy, nitro, cyano, halogen, alkyl, or $N(R^8)(R^9)$, and
  (ii,) $R^8$ and $R^9$ are, independently, $R^{8a}$ where $R^{8a}$ is hydrogen, alkyl, alkenyl, carbocyclic ring, or heterocyclic ring; or $R^8$ and $R^9$ together comprise a heterocyclic ring including the nitrogen to which they are bonded;
(2) $A^2$ is N or $C(R^2)$; where $R^2$ is hydrogen or halogen;
(3) $A^3$ is N or $C(R^5)$; where $R^5$ is hydrogen;
(4) $R^1$ is hydrogen, alkyl, a carbocyclic ring, a heterocyclic ring, alkoxy, hydroxy, alkenyl, arylalkyl, or $N(R^8)(R^9)$;
(5) $R^3$ is hydrogen, halogen, alkyl, a carbocyclic ring, or a heterocyclic ring;

(6) $R^4$ is hydroxy; and (7) $R^6$ is $R^{15}$ or $R^{16}X$; where $R^{15}$ is a substituent moiety of L and is nil, alkyl, heteroalkyl, or alkenyl; $R^{16}$ is a substituent moiety of L and is alkyl, alkenyl, a carbocyclic ring or a heterocyclic ring; and X is alkyl, heteroalkyl, alkenyl, oxygen, sulfur, or NH;

(B) except that (1) when $A^1$ is $C(R^7)$, $R^1$ and $R^7$ may together comprise a heterocyclic ring including N' and $A^1$;

(2) when $A^2$ is $C(R^2)$, $R^2$ and $R^3$ may together comprise —O—$(CH_2)_n$—O—, where n is an integer from 1 to 4;

(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and (4) when $A^3$ is $C(R^5)$, $R^1$ and $R^5$ may together comprise a heterocyclic ring including N' and the adjacent carbon to which $R^5$ is bonded;

(II) B is a structure according to Formula (II), where L is bonded to $R^{14}$:

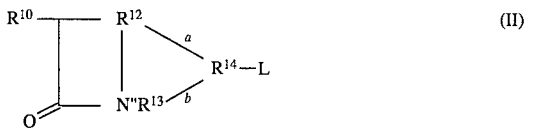

wherein (A) $R^{10}$ is hydrogen, halogen, alkyl, alkenyl, heteroalkyl, a carbocyclic ring, a heterocyclic ring, $R^{8a}$—O—, $R^{8a}CH=N-$, $(R^8)(R^9)N-$, $R^{17}-C(=CHR^{20})-C(=O)NH-$, $R^{17}-C(=NO-R^{19})-C(=O)NH-$, or $R^{18}-(CH_2)_m-C(=O)NH-$; where (1) m is an integer from 0 to 9;

(2) $R^{17}$ is hydrogen, alkyl, alkenyl, heteroalkyl, heteroalkenyl, a carbocyclic ring, or a heterocyclic ring;

(3) $R^{18}$ is $R^{17}$, 13 $Y^1$ or —$CH(Y^2)(R^{17})$;

(4) $R^{19}$ is $R^{17}$, arylalkyl, heteroarylalkyl, —$C(R^{22})(R^{23})COOH$, —$C(=O)O-R^{17}$, or —$C(=O)NH-R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded;

(5) $R^{20}$ is $R^{19}$, halogen, —$Y^1$, or —$CH(Y^2)(R^{17})$;

(6) $Y^1$ is —$C(=O)OR^{21}$, —$C(=O)R^{21}$, —$N(R^{24})R^{21}$, —$S(O)_pR^{29}$, or —$OR^{29}$; and $Y^2$ is $Y^1$ or —OH, —SH, or —$SO_3H$;

(a) p is an integer from 0 to 2;

(b) $R^{24}$ is hydrogen; alkyl; alkenyl; heteroalkyl; heteroalkenyl; a carbocyclic ring; a heterocyclic ring; —$SO_3H$; —$C(=O)R^{25}$; or, when $R^{18}$ is —$CH(N(R^{24})R^{21})(R^{17})$, $R^{24}$ may comprise a moiety bonded to $R^{21}$ to form a heterocyclic ring; and (c) $R^{25}$ is $R^{17}$, $NH(R^{17})$, $N(R^{17})(R^{26})$, $O(R^{26})$, or $S(R^{26})$; where $R^{26}$ is alkyl, alkenyl, a carbocyclic ring, a heterocyclic ring, or when $R^{25}$ is $N(R^{17})(R^{26})$, $R^{26}$ may be a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when $Y^1$ is $N(R^{24})R^{21}$ and $R^{21}$ is $R^{29}$, $R^{21}$ and $R^{24}$ may together comprise a heterocyclic ring including the nitrogen atom to which $R^{24}$ is bonded;

(B) $R^{11}$ is hydrogen, halogen, alkoxy, or $R^{27}C(=O)NH-$, where $R^{27}$ is hydrogen or alkyl;

(C) bond "a" is a single bond or is nil; and bond "b" is a single bond, a double bond, or is nil; except bond "a" and bond "b" are not both nil;

(D) $R^{12}$ is —$C(R^{8a})-$, or —$CH_2-R^{28}-$; where $R^{28}$ is —$C(R^{8a})$, —O—, or —N—, and $R^{28}$ is directly bonded to N" in Formula (II) to form a 5-membered ring; except, if bond "a" is nil, then $R^{12}$ is (1) —$C(R^{8a})(X^1)-$, where (i) $X^1$ is —$R^{21}$; —$OR^{30}$; —$S(O)_rR^{30}$, where r is an integer from 0 to 2; —$O(C=O)R^{30}$; or $N(R^{30})R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) —$CH_2-R^{32}-$; where $R^{32}$ is —$C(R^{8a})(R^{21})$, —O—, or —$NR^{8a}$, and $R^{32}$ is directly bonded to N" in Formula (II) to form a 5-membered ring;

(E) (1) if bond "b" is a single bond, $R^{13}$ is —$CH(R^{33})-$; or, —$C(O)NHSO_2-$, if bond "a" is nil; or —$C^*(R^{33})-$ if $R^{14}$ contains a $R^{36}$ moiety; where $R^{33}$ is hydrogen or COOH, and C* is linked to $R^{36}$ to form a 3-membered ring;

(2) if bond "b" is a double bond, $R^{13}$ is —$C(R^{33})=$; or (3) if bond "b" is nil, $R^{13}$ is hydrogen, —$SO_3H$, —$PO(OR^{34})OH$, —$C(O)NHSO_2N(R^{34})(R^{35})$, —$OSO_3H$, —$CH(R^{35})COOH$, or —$OCH(R^{34})COOH$; where $R^{34}$ is hydrogen, alkyl, alkenyl, a carbocyclic ring, or a heterocyclic ring; and $R^{35}$ is hydrogen, alkyl, alkenyl, or —$NHR^{8a}$; or, if $R^{13}$ is —$C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil and L is bonded directly to $R^{12}$ or $R^{13}$;

(2) if bond "a" and "b" are single bonds, $R^{14}$ is —W—C'''=$C(R^{8a})$—$R^{37}$—, or —W—C'''($R^{36}$)—$R^{37}$—; or (3) if bond "a" is a single bond and bond "b" is a double bond, $R^{14}$ is —$C(R^{8a})(R^{38})$—W—C'''—$R^{37}$—; —W—$C(R^{8a})(R^{38})$—C'''—$R^{37}$—; or —W—C'''—$R^{37}$—; where (a) W is O; $S(O)_s$, where s is an integer from 0 to 2; or $C(R^{38})$, where $R^{38}$ is hydrogen, alkyl or alkoxy;

(b) $R^{36}$ hydrogen; alkyl; alkenyl; —COOH; or, if $R^{13}$ is —$C^*(R^{33})$, $R^{36}$ may be linked to C* to form a 3-membered carbocyclic ring;

(c) $R^{37}$ is nil, alkyl, alkenyl, a carbocyclic ring, or a heterocyclic ring; and (d) C''' is directly bonded to $R^{13}$ to form a 5- or 6-membered ring, and (III) L links Q to B; and L is L', —$X^2_t$—$R^{39}$—L', or —$X^3_t$—$R^{39}$—L', where L' is Q', —$X^2$—Q", or —$X^3$—Q", —$X^4_t$—$C(=Y^3_u)$—Z—Q";

(1) t and u are, independently, 0 or 1;

(2) $R^{39}$ is alkyl, alkenyl, heteroalkyl, heteroalkenyl, a carbocyclic ring, or a heterocyclic ring;

(3) $X^2$ is oxygen, or $S(O)_v$, where v is an integer from 0 to 2;

(4) $X^3$ is nitrogen; $N(R^{40})$; $N^+(R^{41})(R^{42})$; or $R^{43}$—$N(R^{41})$; and is linked to $R^{14}$ by a single or double bond; or, if $R^{14}$ is nil, $X^3$ is linked to B by a single or double bond; where (a) $R^{40}$ is $R^{8a}$; —$OR^{8a}$; or —$C(=O)R^{8a}$;

(b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q" may comprise a heterocyclic ring as $R^{16}$;

(c) $R^{43}$ is $N(R^{41})$, oxygen or sulfur;

(5) $X^4$ is oxygen, sulfur, $NR^{40}$, or $R^{43}$—$NR^{41}$;

(6) $Y^3$ is oxygen, sulfur, $NR^{40}$ or $N^+(R^{41})(R^{42})$;

(7) $Y^4$ is oxygen or $NR^{41}$;

(8) Z is nil, oxygen, sulfur, nitrogen, $NR^{40}$, or $N(R^{41})$—$R^{43}$;

(9) Q' is said $R^6$ substituent of Q; and

(10) Q" is Q'; or together with $X^2$, $X^3$, or Z, is said $R^6$ substituent of Q;

and pharmaceutically-acceptable salts and biohydrolyzable esters thereof, and hydrates thereof.

It has been found that the compounds of this invention, and compositions containing these compounds, are effective antimicrobial agents against a broad range of pathogenic microorganisms. These compounds provide advantages versus antimicrobial agents among those known in the art, including (for example) the spectrum of antimicrobial activity, potency, the avoidance of microbial resistance, reduced toxicity, and improved pharmacology.

DESCRIPTION OF THE INVENTION

The present invention encompasses certain novel lactam-quinolones, methods for their manufacture, dosage forms, and methods of administering the lactam-quinolones to a human or other animal subject. Specific compounds and compositions to be used in the invention must, accordingly, be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

Quinolonyl Lactams

The compounds of this invention, herein referred to as "quinolonyl lactams", encompass any of a variety of lactam moieties linked, by a linking moiety, to a quinolone moiety at the 5-position of the quinolone. These compounds include those having the general formula

wherein Q, L and B are defined as follows:

(I) Q is a structure according to Formula (I)

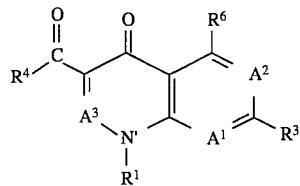

wherein (A) (1) $A^1$ is N or $C(R^7)$; where (i) $R^7$ is hydrogen, hydroxy, alkoxy, nitro, cyano, halogen, alkyl, or $N(R^8)(R^9)$ (preferably hydrogen or halogen), and (ii) $R^8$ and $R^9$ are, independently, $R^{8a}$, where $R^{8a}$ is hydrogen, alkyl, alkenyl, carbocyclic ring, or heterocyclic ring substituents; or $R^8$ and $R^9$ together comprise a heterocyclic ring including the nitrogen to which they are bonded;

(2) $A^2$ is N or $C(R^2)$ (preferably $C(R^2)$); where $R^2$ is hydrogen or halogen;

(3) $A^3$ is N or (preferably) $C(R^5)$; where $R^5$ is hydrogen;

(4) $R^1$ is hydrogen, alkyl, a carbocyclic ring, heterocyclic ring, alkoxy, hydroxy, alkenyl, arylalkyl, or $N(R^8)(R^9)$ (preferably alkyl or a carbocyclic ring);

(5) $R^3$ is hydrogen, halogen, alkyl, a carbocyclic ring, or a heterocyclic ring (preferably a heterocyclic ring);

(6) $R^4$ is hydroxy; and (7) $R^6$ is $R^{15}$ or $R^{16}X$; where $R^{15}$ is a substituent moiety of L and is nil, alkyl, heteroalkyl, or alkenyl; $R^{16}$ is a substituent moiety of L and is alkyl, alkenyl, a carbocyclic ring or a heterocyclic ring; and X is alkyl, heteroalkyl, alkenyl, oxygen, sulfur, or NH;

(B) except that (1) when $A^1$ is $C(R^7)$, $R^1$ and $R^7$ may together comprise heterocyclic ring including N' and $A^1$;

(2) when $A^2$ is $C(R^2)$, $R^2$ and $R^3$ may together comprise —O—$(CH_2)_n$—O—, where n is an integer from 1 to 4;

(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and (4) when $A^3$ is $C(R^5)$, $R^1$ and $R^5$ may together comprise a heterocyclic ring including N' and the adjacent carbon to which $R^5$ is bonded;

(II) B is a structure according to Formula (II), where L is bonded to $R^{14}$:

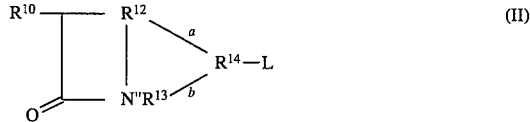

wherein (A) $R^{10}$ is hydrogen, halogen, heteroalkyl, a carbocyclic ring, a heterocyclic ring, $R^{8a}$—O—, $R^{8a}CH=N$—, $(R^8)(R^9)N$—, $R^{17}$—C(=CHR$^{20}$)—C(=O)NH—, or (preferably) alkyl, alkenyl, $R^{17}$—C(=NO—R$^{19}$)—C(=O)NH—, or $R^{18}$—$(CH_2)_m$—C(=O)NH—; where (1) m is an integer from 0 to 9 (preferably from 0 to 3);

(2) $R^{17}$ is hydrogen, alkyl, alkenyl, heteroalkyl, heteroalkenyl, a carbocyclic ring, or a heterocyclic ring (preferably alkyl, a carbocyclic ring, or a heterocyclic ring);

(3) $R^{18}$ is $R^{17}$, —$Y^1$, or —CH($Y^2$)($R^{17}$);

(4) $R^{19}$ is $R^{17}$, arylalkyl, heteroarylalkyl, —C($R^{22}$)($R^{23}$)COOH, —C(=O)O—$R^{17}$, or —C(=O)NH—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded (preferably $R^{17}$ or —C($R^{22}$)($R^{23}$)COOH)

(5) $R^{20}$ is $R^{19}$, halogen, —$Y^1$, or —CH($Y^2$)($R^{17}$) (preferably $R^{19}$ or halogen);

(6) $Y^1$ is —C(=O)O$R^{21}$, —C(=O)$R^{21}$, —N($R^{24}$)$R^{21}$, or —S(O)$_p$$R^{29}$ or —O$R^{29}$; and $Y^2$ is $Y^1$ or —OH, —SH, or —SO$_3$H;

(a) p is an integer from 0 to 2 (preferably 0);

(b) $R^{24}$ is hydrogen; alkyl; alkenyl; heteroalkyl; heteroalkenyl; a carbocyclic ring; a heterocyclic ring; —SO$_3$H; —C(=O)$R^{25}$; or, when $R^{18}$ is —CH(N($R^{24}$)$R^{21}$)($R^{17}$), $R^{24}$ may comprise a moiety bonded to $R^{21}$ to form a heterocyclic ring; and (c) $R^{25}$ is $R^{17}$, NH($R^{17}$), N($R^{17}$)($R^{26}$), O($R^{26}$), or S($R^{26}$) (preferably $R^{17}$, NH($R^{17}$) or N($R^{17}$)($R^{26}$)); where $R^{26}$ is alkyl, alkenyl, a carbocyclic ring, a heterocyclic ring or (preferably) when $R^{25}$ is N($R^{17}$)($R^{26}$), $R^{26}$ may comprise a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when $Y^1$ is N($R^{24}$)$R^{21}$ and $R^{21}$ is $R^{29}$, $R^{21}$ and $R^{24}$ may together comprise a heterocyclic ring including the nitrogen atom to which $R^{24}$ is bonded (preferably hydrogen, alkyl, a carbocyclic ring or a heterocyclic ring);

(B) $R^{11}$ is hydrogen, halogen, alkoxy, or $R^{27}C(=O)NH$— preferably hydrogen or alkoxy), where $R^{27}$ is hydrogen or alkyl (preferably hydrogen);

(C) bond "a" is a single bond or is nil; and bond "b" is a single bond, a double bond, or is nil; except bond "a" and bond "b" are not both nil;

(D) $R^{12}$ is —$C(R^{8a})$—, or —$CH_2$—$R^{28}$— (preferably —$C(R^{8a})$—); where $R^{28}$ is —$C(R^{8a})$, —O—, or —N—, and $R^{28}$ is directly bonded to N" in Formula (II) to form a 5-membered ring; except, if bond "a" is nil, then $R^{12}$ is (1) (preferably) —$C(R^{8a})(X^1)$—, where (i) $X^1$ is —$R^{21}$; —$OR^{30}$; —$S(O)_rR^{30}$, where r is an integer from 0 to 2 (preferably 0); —$O(C=O)R^{30}$; or $N(R^{30})R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) —$CH_2$—$R^{32}$—; where $R^{32}$ is —$C(R^{8a})(R^{21})$, —O—, or —$NR^{81}$, and $R^{32}$ is directly bonded to N" in Formula (II) to form a 5-membered ring;

(E) (1) if bond "b" is a single bond, $R^{13}$ is preferably —$CH(R^{33})$—; or, —$C(O)NHSO_2$—, if bond "a" is nil; or —$C*(R^{33})$—, if $R^{14}$ contains a $R^{36}$ moiety; where $R^{33}$ is hydrogen or COOH (preferably COOH), and C* is linked to $R^{36}$ to form a 3-membered ring;

(2) if bond "b" is a double bond, $R^{13}$ is —$C(R^{33})=$; or (3) if bond "b" is nil, $R^{13}$ is hydrogen, —$SO_3H$, —$PO(OR^{34})OH$, —$C(O)NHSO_2N(R^{34})(R^{35})$, —$OSO_3H$, —$CH(R^{35})COOH$, or —$OCH(R^{34})COOH$ (preferably —$SO_3H$, or —$C(O)NHSO_2N(R^{34})(R^{35})$; where $R^{34}$ is hydrogen, alkyl, alkenyl, a carbocyclic ring, or a heterocyclic ring; and $R^{35}$ is hydrogen, alkyl, alkenyl, or —$NHR^{8a}$; or (preferably), if $R^{13}$ is —$C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil and L is bonded directly to $R^{12}$ or $R^{13}$;

(2) if bond "a" and "b" are single bonds, $R^{14}$ is —W—C'''=C($R^{8a}$)—$R^{37}$—, or —W—C'''($R^{36}$)—$R^{37}$—; or (3) (preferably) if bond "a" is a single bond and bond "b" is a double bond, $R^{14}$ is —$C(R^{8a})(R^{38})$—W—C'''—$R^{37}$—; or (preferably) —W—$C(R^{8a})(R^{38})$—C'''—$R^{37}$—, or —W—C'''—$R^{37}$—;

where (a) W is O; $S(O)_s$, where s is an integer from 0 to 2 (preferably 0); or $C(R^{38})$, where $R^{38}$ is hydrogen, alkyl or alkoxy;

(b) $R^{36}$ hydrogen; alkyl; alkenyl; —COOH; or, if $R^{13}$ is —$C*(R^{33})$, $R^{36}$ may be linked to C* to form a 3-membered carbocyclic ring;

(c) $R^{37}$ is nil, alkyl, alkenyl, a carbocyclic ring, or a heterocyclic ring; and (d) C''' is directly bonded to $R^{13}$ to form a 5- or 6-membered ring, and (III) L links Q to B; and L is L', —$X^2_t$—$R^{39}$—L', or —$X^3_t$—$R^{39}$—L', where L' is Q', —$X^2$—Q", —$X^3$—Q", or —$X^4_t$—$C(=Y^3_u)$—Z—Q" (preferably —$X^2$—Q", —$X^3$—Q", —$X^4_t$—$C(=Y^3_u)$—Z—Q");

(1) t and u are, independently, 0 or 1;

(2) $R^{39}$ is alkyl, alkenyl, heteroalkyl, heteroalkenyl, a carbocyclic ring, or a heterocyclic ring (preferably alkyl or alkenyl);

(3) $X^2$ is oxygen, or $S(O)_v$, where v is an integer from 0 to 2 (preferably 0);

(4) $X^3$ is nitrogen; $N(R^{40})$; $N^+(R^{41})(R^{42})$; or $R^{43}$—$N(R^{41})$; and is linked to $R^{14}$ by a single or double bond; or, if $R^{14}$ is nil, $X^3$ is linked to B by a single or double bond (preferably $X^3$ is nitrogen, $N(R^{40})$ or $N^+(R^{41})(R^{42})$); where (a) $R^{40}$ is $R^{8a}$; —$OR^{8a}$; or —$C(=O)R^{8a}$; (preferably $R^{8a}$);

(b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q", may comprise a heterocyclic ring as $R^{16}$;

(c) $R^{43}$ is $N(R^{41})$, oxygen or sulfur;

(5) $X^4$ is oxygen, sulfur, $NR^{40}$, or $R^{43}$—$NR^{41}$ (preferably oxygen, sulfur or $NR^{40}$);

(6) $Y^3$ is oxygen, sulfur, $NR^{40}$ or $N^+(R^{41})(R^{42})$;

(7) $Y^4$ is oxygen or $NR^{41}$ (preferably oxygen);

(8) Z is nil, oxygen, sulfur, nitrogen, $NR^{40}$, or $N(R^{41})$—$R^{43}$ (preferably oxygen, sulfur, nitrogen or $NR^{40}$);

(9) Q' is said $R^6$ substituent of Q; and

(10) Q" is Q'; or together with $X^2$, $X^3$, Z or Z', is said $R^6$ substituent of Q;

and pharmaceutically-acceptable salts and biohydrolyzable esters thereof, and hydrates thereof.

Definitions and Usage of Terms:

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, quinolinyl, pyrimidinyl and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred arylalkyl groups include benzyl and phenylethyl.

"Arylamino" is an amine radical substituted with an aryl group ( i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkylacyl groups include (for example) acetyl, formyl, and propionyl.

"Acyloxy" is an oxygen radical having an acyl substituent ( i.e., —O—acyl); for example, —O—C(=O)—alkyl.

"Acylamino" is an amino radical having an acyl substituent ( i.e., —N—acyl); for example, —NH—C(=O)—alkyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a quinolonyl lactam that does not essentially interfere with the antimicrobial activity of the compounds, or that are readily metabolized by a human or lower animal subject to yield an antimicrobially-active quinolonyl lactam. Such esters include those that do not interfere with the biological activity of quinolone antimicrobials or beta-lactam antimicrobials (cephems, for example). Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

As defined above and as used herein, substituent groups may themselves be substituted. Such substitution may be with one or more substituents. Such substituents include (for example) those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^{8a}$ substituent is defined as a potential substituent of $R^7$, but is also incorporated into the definition of other substituents (such as $R^6$, $R^{12}$, $R^{32}$ and L'). As used herein, such a radical is independently selected each time it is used (e.g., $R^{8a}$ need not be alkyl in all occurrences in defining a given compound of this invention).

Lactam-containing moiety:

Groups $R^{12}$, $R^{13}$, and $R^{14}$, together with bonds "a" and "b" of formula (I), form any of a variety of lactam-containing moieties known in the art to have antimicrobial activity. Such moieties wherein either bond "a" or bond "b" are nil (i.e., do not exist) are mono-cyclic; if both bonds exist, the structures are bi-cyclic. Preferably, bond "a" is a single bond and bond "b" is a double bond.

Preferred lactam moieties include the cephems, oxacephems and carbacephems of the representative formula:

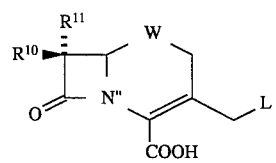

wherein, referring to formula (II), bond "a" is a single bond; bond "b" is a double bond; $R^{12}$ is —C($R^{8a}$)—, where $R^{8a}$ is hydrogen; $R^{13}$ is —CH($R^{33}$), where $R^{33}$ is COOH; and $R^{14}$ is —W—C($R^{8a}$)($R^{38}$)—C'''—$R^{37}$, where $R^{8a}$ and $R^{38}$ are hydrogen, $R^{37}$ is methylene, and W is S (for cephems), O (for oxacephems) or C($R^{38}$) (for carbacephems).

Other preferred lactam moieties include the isocephems and iso-oxacephems of the representative formula:

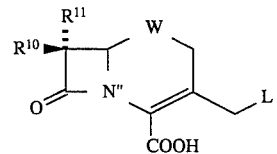

wherein, referring to formula II, bond "a" is a single bond; bond "b" is a double bond; $R^{12}$ is —C($R^{8a}$) where $R^{8a}$ is hydrogen; $R^{13}$ is —C($R^{33}$)=, where $R^{33}$ is COOH; and $R^{14}$ is —C($R^{8a}$)($R^{38}$)—W—C'''—$R^{37}$ where $R^{8a}$ and $R^{38}$ are each hydrogen, $R^{37}$ is methylene, and W is S (for isocephems) or O (for iso-oxacephems).

Other preferred lactam-containing moieties include the penems, carbapenems and clavems, of the representative formula:

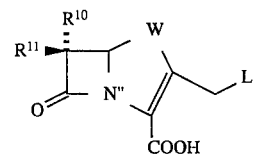

wherein, referring to formula (II), bond "a" is a single bond; bond "b" is a double bond; $R^{12}$ is —C($R^{8a}$), where $R^{8a}$ is hydrogen; $R^{13}$ is —C($R^{33}$)=, where $R^{33}$ is COOH; and $R^{14}$ is —W—C'''—$R^{37}$, where $R^{37}$ is methylene, and W is S (for penems), C($R^{38}$) (for carbapenems), or O (for clavems). Such lactam moieties are described in the following articles, all incorporated by reference herein: R. Wise, "In Vitro and Pharmacokinetic Properties of the Carbapenems", 30 *Antimicrobial Agents and Chemotherapy* 343 (1986); and S. McCombie et al., "Synthesis and In Vitro Activity of the Penem Antibiotics", 8 *Medicinal Research Reviews* 393 (1988).

Other preferred lactam-containing moieties of this invention include the penicillins of the representative formula:

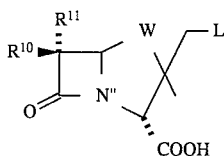

wherein, referring to formula II, bond "a" is a single bond, bond "b" is a single bond; $R^{12}$ is —$C(R^{8a})$—, where $R^{8a}$ is hydrogen; $R^{13}$ is —$CH(R^{33})$— where $R^{33}$ is COOH; and $R^{14}$ is —W—$C'''(R^{36})$—$R^{37}$— where $R^{36}$ is methyl, $R^{37}$ is methylene, and W is S.

Other preferred lactam-containing moieties include the monocyclic beta-lactams, of the representative formula:

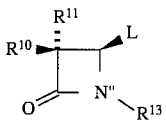

wherein, referring to formula (II), bond "a" is a single bond; bond "b" is nil; $R^{12}$ is —$C(R^{8a})$—, where $R^{8a}$ is hydrogen; $R^{14}$ is nil; and $R^{13}$ is —$SO_3H$ (for a monobactam), —$PO(OR^{34})OH$ (for a monophospham); —$C(O)NHSO_2N(R^{34})(R^{35})$ (for a monocarbam), —$OSO_3H$ (for a monosulfactam), —$CH(R^{35})COOH$ (for nocardicins), or —$OCH(R^{34})COOH$. Such lactam moieties are described in C. Cimarusti et al., "Monocyclic 8-lactam Antibiotics", 4 *Medicinal Research Reviews* 1 (1984), incorporated by reference herein.

Other preferred lactam moieties include the monocyclic beta-lactams of the representative formula:

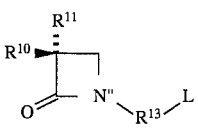

wherein referring to formula II, bond "a" is nil, bond "b" is a single bond; $R^{12}$ is —$C(R^{8a})(R^{29})$— where both $R^{8a}$ and $R^{29}$ are hydrogen; and $R^{14}$ is nil.

Other preferred lactam moieties include the clavams of the representative formula:

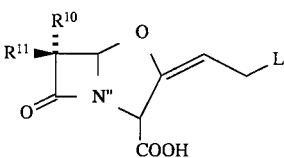

wherein, referring to formula (II), bond "a" is a single bond; bond "b" is a single bond; $R^{12}$ is —$C(R^{8a})$—, where $R^{8a}$ is hydrogen; $R^{13}$ is —$CH(R^{33})$—, where $R^{33}$ is COOH; and $R^{14}$ is W—$C'''$=C—$(R^{8a})$—$R^{37}$, where $R^{8a}$ is hydrogen and $R^{37}$ is methylene, and W is O.

Other preferred lactam moieties include the 2,3-methylenopenams and -carbapenams of the representative formula:

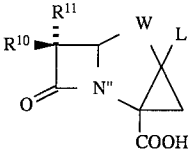

wherein, referring to formula (II), bond "a" is a single bond; bond "b" is a single bond; $R^{12}$ is —$C(R^{8a})$—, where $R^{8a}$ is hydrogen; $R^{13}$ is —$C^*(R^{33})$, where $R^{33}$ is COOH; and $R^{14}$ is W—$C'''(R^{36})$—$R^{37}$, where $R^{37}$ is nil, $R^{36}$ is linked to $C^*$ to form a 3-membered carbocyclic ring, and W is $C(R^{38})$ or sulfur.

Lactam moieties of this invention also include the lactivicin analogs of the representative formula:

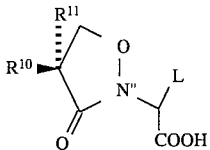

wherein, referring to formula (II), bond "a" is nil; bond "b" is a single bond; $R^{12}$ is —$CH_2$—$R^{32}$, where $R^{32}$ is O; $R^{13}$ is —$CH(R^{33})$—, where $R^{33}$ is COOH; and $R^{14}$ is nil.

Other lactam moieties include the pyrazolidinones of the representative formula:

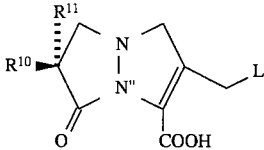

wherein, referring to formula (I), bond "a" is a single bond; bond "b" is a double bond; $R^{12}$ is —$CH_2$—$R^{28}$—, where $R^{28}$ is —N—; $R^{13}$ is —$C(R^{33})$—, where $R^{33}$ is COOH; and $R^{14}$ is W—$C'''$—$R^{37}$—, where $R^{37}$ is methylene, and W is $C(R^{38})$.

Other lactam moieties include the gamma-lactams of the representative formula:

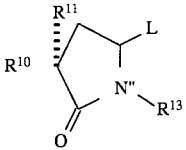

wherein, referring to formula (II), bond "a" is a single bond; bond "b" is nil; $R^{12}$ is —$CH_2$—$R^{28}$—, where $R^{28}$ is —$C(R^{8a})$— and $R^{8a}$ is hydrogen; $R^{13}$ is —$SO_3H$, —$PO(OR^{34})OH$, —$C(O)NHSO_2N(R^{34})(R^{35})$, —$OSO_3H$, —$CH(R^{35})COOH$, or —$OCH(R^{34})COOH$; and $R^{14}$ is nil.

Preferred lactam-containing moieties include cephems, isocephems, iso-oxacephems, oxacephems, carbacephems, penicillins, penems, carbapenems, and monocyclic beta-lactams. Particularly preferred are cephems, penems, carbapenems and monocyclic beta-lactams.

$R^{10}$, in formula (II), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity. ) This "active" position is beta ( i.e., 7-beta) for cephems, oxacephems and carbacephems (for example). The active position is alpha for penems, carbapenems, clavems and clavams.

Appropriate $R^{10}$ groups will be apparent to one of ordinary skill in the art. Many such $R^{10}$ groups are known in the art, as described in the following documents (all of which are incorporated by reference herein): *Cephalosporins and Penicillins: Chemistry and Biology* (E. Flynn, editor, 1972); *Chemistry and Biology of b-Lactam Antibiotics* (R. Morin et al., editors, 1987); "The Cephalosporin Antibiotics: Seminar-in-Print", 34 Drugs (Supp. 2) 1 (J. Williams, editor, 1987); *New Beta-Lactam Antibiotics: A Review from Chemistry of Clinical Efficacy of the New Cephalosporins* (H. Neu, editor, 1982); M. Sassiver et al., in *Structure Activity Relationships among the Semi-synthetic Antibiotics* (D. Perlman, editor, 1977). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavams, $R^{10}$ is preferably lower alkyl, or hydroxy-substituted lower alkyl. Particularly preferred $R^{10}$ groups include hydrogen, hydroxymethyl, ethyl, [1(R)-hydroxyethyl], [1(R)-[(hydroxysulfonyl)oxyethyl]], and [1-methyl-1-hydroxyethyl].

Except for penems, carbapenems, clavems and clavams, preferred $R^{10}$ groups are amides, such as: acetylamino, preferably substituted with aryl, heteroaryl, aryloxy, heteroarylthio and lower alkylthio substituents; arylglycylamino, preferably N-substituted with heteroarylcarbonyl and cycloheteroalkylcarbonyl substituents; arylcarbonylamino; heteroarylcarbonylamino; and lower alkoxyiminoacetylamino, preferably substituted with aryl and heteroaryl substituents. Particularly preferred $R^{10}$ groups include amides of the general formula $R^{18}$—$(CH_2)_m$—$C(=O)NH$— and $R^{18}$ is $R^{17}$. Examples of such preferred $R^{10}$ groups include:

[(2-amino-5-halo-4-thiazolyl)acetyl)amino;

[(4-aminopyridin-2-yl)acetyl]amino;

[[(3,5-dichloro-4-oxo-1(4H)-pyridinyl)acetyl]amino);

[[[2-(aminomethyl)phenyl]acetyl]amino];

[(1H-tetrazol-1-ylacetyl)amino];

[(cyanoacetyl)amino];

[(2-thienylacetyl)amino];

[[(2-amino-4-thiazoyl)acetyl]amino); and sydnone, 3-[-2-amino]-2-oxoethyl.

The following are other such preferred $R^{10}$ groups.

HCONH—

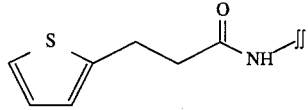

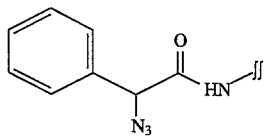

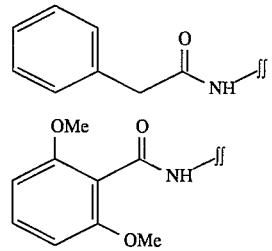

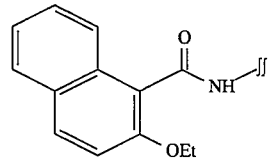

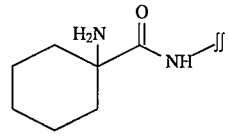

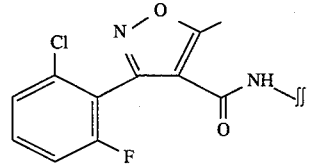

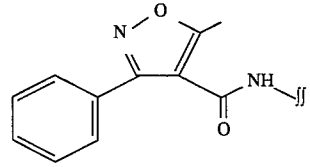

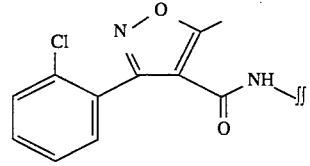

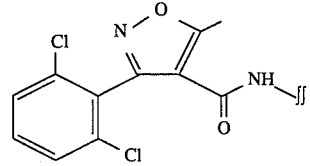

When $R^{10}$ is $R^{18}$—$(CH_2)_m$—$C(C=O)NH$—, and $R^{18}$ is —$Y^1$, preferred $R^{10}$ groups include the following:

[sulfamoylphenylacetyl]amino;

[[(4-pyridinylthio)acetyl]amino];

[[[(cyanomethyl)thio]acetyl]amino];

(S)-[[[(2-amino-2-carboxyethyl)thio]acetyl]amino];

[[[(trifluoromethyl)thio]acetyl]amino]; and (E)-[[[(2-aminocarbonyl-2-fluoroethenyl)thio]acetyl]amino].

The following are other such preferred $R^{10}$ groups.

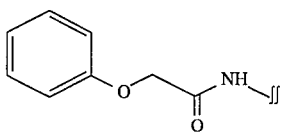

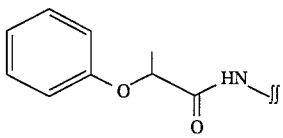

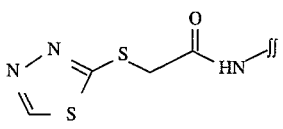

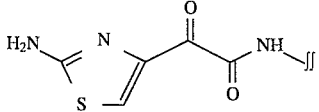

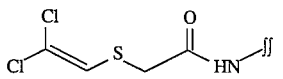

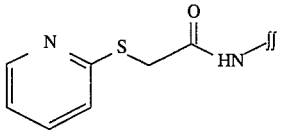

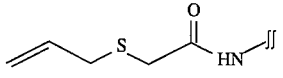

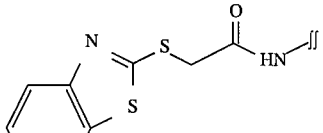

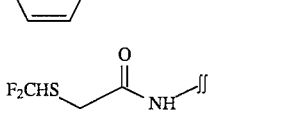

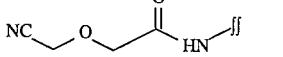

When $R^{10}$ is $R^{18}$—$(CH_2)_m$—$C(=O)NH$—, and $R^{18}$ is —$CH(Y^2)(R^{17})$, preferred $R^{10}$ groups include the
[carboxyphenylacetyl]amino;
[(phenoxycarbonyl)phenylacetyl]amino;
[4-methyl-2,3-dioxo-1-piperazinecarbonyl-D-phenylglycyl]-amino;
[[[3-(2-furylmethyleneamino)-2-oxo-1-imidazolidinyl]-carbonyl]amino]phenyl]acetyl]amino;
(R)-[(aminophenylacetyl)amino];
(R)-[[amino(4-hydroxyphenyl)acetyl]amino];
(R)-[(amino-1,4-cyclohexadien-1-ylacetyl)amino];
[(hydroxyphenylacetyl)amino];
(R)-[[[[(4-ethyl-2,3-dioxo-1-piperazinyl)carbonyl]amino]-(4-hydroxyphenyl)acetyl]amino];
(R)-[[[[(5-carboxy-1H-imidazol-4-yl)carbonyl]amino]phenylacetyl]amino);
(R)-[[[[(4-hydroxy-6-methyl-3-pyridinyl)carbonyl]amino](4-hydroxyphenyl)acetyl]amino];
(R)-[(phenylsulfoacetyl)amino];
(2R,3S)-[[2-[[(4-ethyl-2,3-dioxo-1-piperazinyl)carbonyl]amino]-3-hydroxy-1-oxobutyl]amino];
[[carboxy(4-hydroxyphenyl)acetyl]amino];
(R)-[[amino[3-[(ethylsulfonyl)amino]phenyl]acetyl]amino];
(R)-[[amino(benzo[b]thien-3-yl)acetyl]amino];
(R)-[[amino(2-naphthyl)acetyl]amino];
(R)-[[amino(2-amino-4-thiazolyl)acetyl]amino];
[[[[(6,7-dihydroxy-4-oxo-4H-1-benzopyran-3-yl)carbonyl]-amino](4-hydroxyphenyl)acetyl]amino];
(R,R)-[[2-[4-[2-amino-2-carboxyethyloxycarbonyl]aminophenyl]-2- hydroxyacetyl]amino]; and
(S)-[[(5-hydroxy-4-oxo-1(4H)-pyridin-2-yl)carbonylamino(2-amino-4-thiazolyl)acetyl]amino].

The following are other such preferred $R^{10}$ groups.

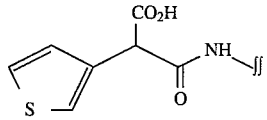

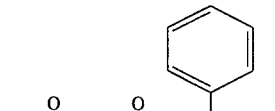

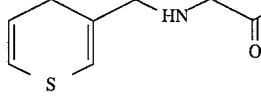

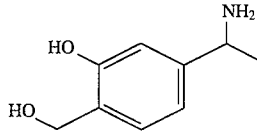

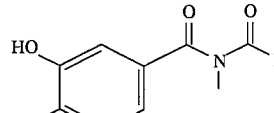

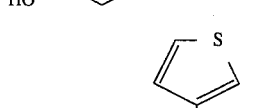

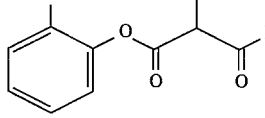

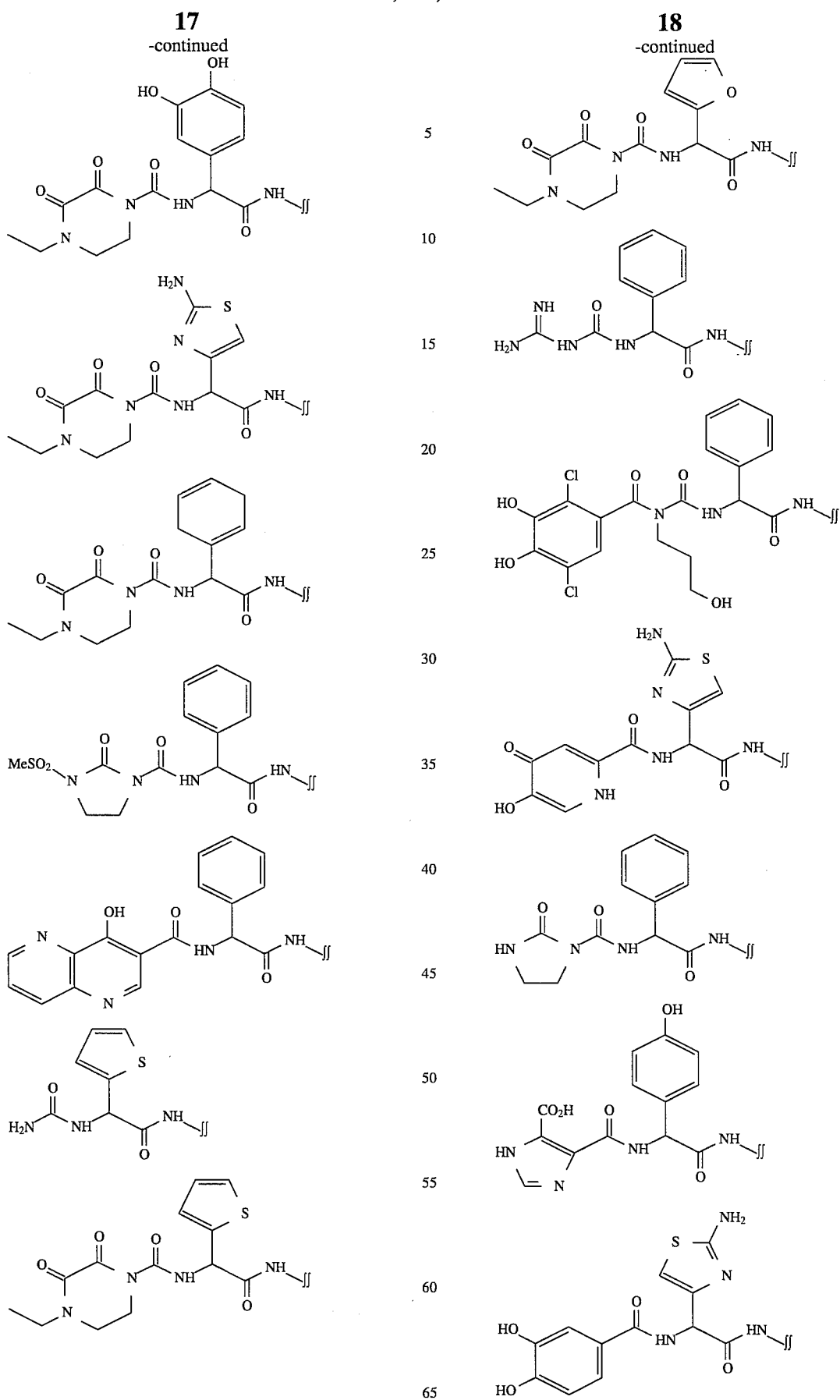

Another preferred $R^{10}$ group is $R^{17}$—C(=CHR$^{20}$)—C(=O)NH—. Such groups include (for example) the following structures.

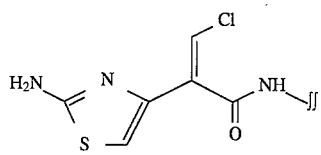

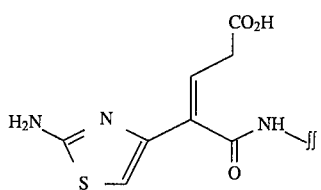

Another class of preferred $R^{10}$ groups (for lactam-containing moieties other than penems, carbapenems, clavems and clavams) include those of the formula:

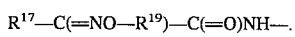

Examples of this preferred class of $R^{10}$ groups include:

2-phenyl-2-hydroxyiminoacetyl;

2-thienyl-2-methoxyiminoacetyl; and

2-[4-gamma-D-glutamyloxy)phenyl]-2-hydroxyiminoacetyl.

(Z)[[(2-amino-4-thiazolyl)(methoxyimino)acetyl]amino];

[[(2-furanyl(methoxyimino)acetyl]amino];

(Z)-[[(2-amino-4-thiazolyl)[(1-carboxy-1-methyl)ethoxyimino]acetyl]amino ];

(Z)-[[(2-amino-4-thiazolyl)(1-carboxymethoxyimino)acetyl]amino];

[[(2-amino-4-thiazolyl)[(1H-imidazol-4-ylmethoxY)imino]acetyl]amino];

(Z)-[[(2-amino-4-thiazolyl-3-oxide)(methoxyimino)acetyl]amino]; and (S,Z)-[[(2-amino-4-thiazolyl)[carboxy(3,4-dihydroxyphenyl)methoxyimino]acetyl]amino].

Other preferred $R^{10}$ groups include the following structures (where "SS" is HCONH—).

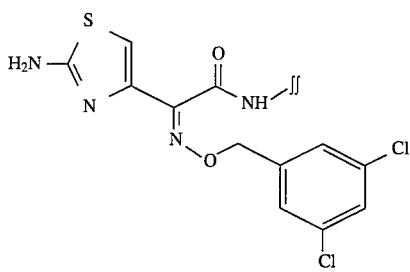

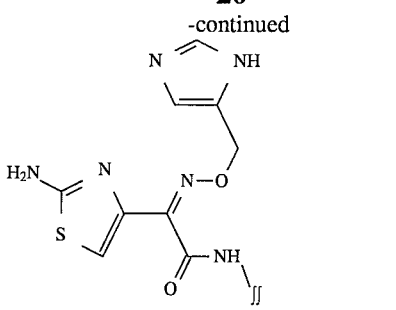

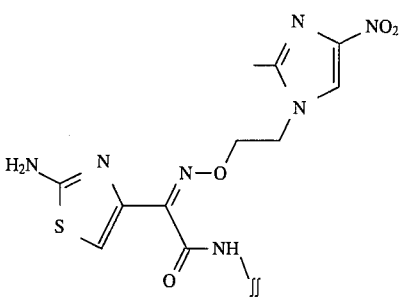

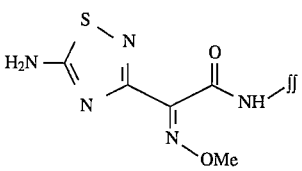

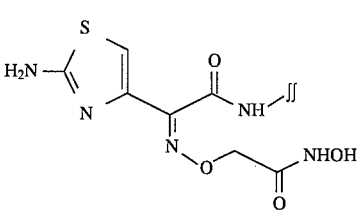

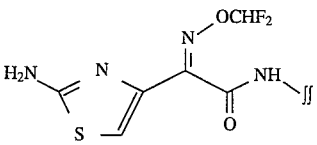

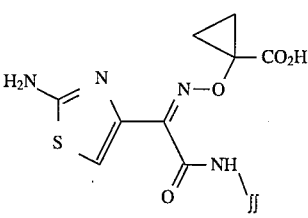

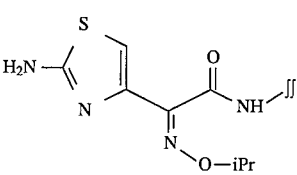

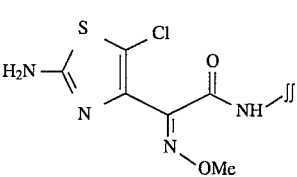

-continued

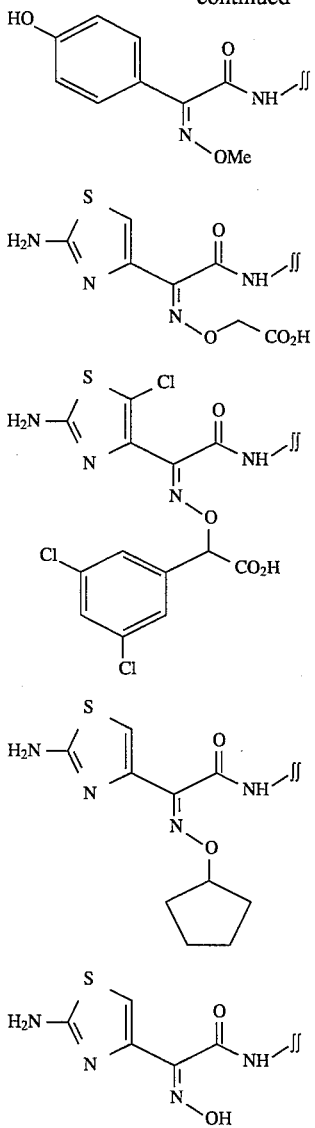

The following are other preferred $R^{10}$ groups.

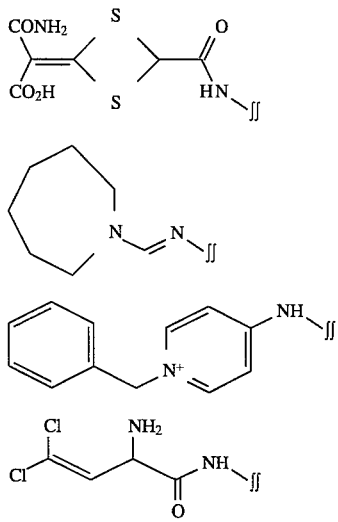

Suitable $R^{11}$ groups are among those well-known in the art, including those defined in the following documents (all incorporated by reference herein). W. Durckheimer et al., "Recent Developments in the Field of Beta-Lactam Antibiotics", 24 Angew. Chem, Int. Ed. Engl. 180 (1985); G. Rolinson, "Beta-Lactam Antibiotics", 17 J. Antimicrobial Chemotherapy 5 (1986); and European Patent Publication 187,456, Jung, published Jul. 16, 1986. Preferred $R^{11}$ groups include hydrogen, methoxy, ethoxy, propoxy, thiomethyl, halogen, cyano, formyl and formylamino. Particularly preferred $R^{11}$ groups include hydrogen, methoxy, halogen, and formylamino.

Quinolone Moieties:

Groups $A^1$, $A^2$, $A^3$, $R^1$, $R^3$, and $R^4$ of formula I form a moiety (herein, "core quinolone moiety") present in any of a variety of quinolone, naphthyridine or related heterocyclic moieties known in the art to have antimicrobial activity. Such heterocyclic moieties are well known in the art, as described in the following articles, all incorporated by reference herein: J. Wolfson et al., "The Fluoroquinolones: Structures, Mechanisms of Action and Resistance, and Spectra of Activity In Vitro", 28 Antimicrobial Agents and Chemotherapy 581 (1985); and T. Rosen et al., 31 J. Med Chem. 1586 (1988); T. Rosen et al., 31 J. Med. Chem. 1598 (1988); G. Klopman et al., 31 Antimicrob. Agents Chemother. 1831 (1987); 31:1831–1840; J. P. Sanchez et al., 31 J. Med. Chem. 983 (1988); J. M. Domagala et al., 31 J. Med. Chem. 991 (1988); M. P. Wentland et al., in 20 Ann. Rep. Med. Chem. 145 (D. M. Baily, editor, 1986); J. B. Cornett et al., in 21 Ann. Rep. Med. Chem. 139 (D. M. Bailey, editor, 1986); P. B. Fernandes et al., in 22 Ann. Rep. Med. Chem. 117 (D. M. Bailey, editor, 1987); R. Albrecht, 21 Prog. Drug Research 9 (1977); and P. B. Fernandes et al., in 23 Ann. Rep. Med. Chem. (R. C. Allen, editor, 1987).

Preferred quinolone moieties include those where $A^1$ is $C(R^7)$, $A^2$ is $C(R^2)$, and $A^3$ is $C(R^5)$ (i.e., quinolones); $A^1$ is nitrogen, $A^2$ is $C(R^2)$, and $A^3$ is $C(R^5)$ (i.e., naphthyridines); $A^1$ is $C(R^7)$, $A^2$ is $C(R^2)$, and $A^3$ is nitrogen (i.e., cinnoline acid derivatives); and where $A^1$ is nitrogen, $A^2$ is nitrogen, and $A^3$ is $C(R^5)$ (i.e., pyridopyrimidine derivatives). More preferred quinolone moieties are those where $A^1$ is $C(R^7)$, $A^2$ is $C(R^2)$, and $A^3$ is $C(R^5)$ (i.e., quinolones); and where $A^1$ is nitrogen, $A^2$ is $C(R^2)$, and $A^3$ is $C(R^5)$ (i.e., naphthyridines). Particularly preferred quinolone moieties are where $A^1$ is $C(R^7)$, $A^2$ is $C(R^2)$, and $A^3$ is $C(R^5)$ (i.e., quinolones).

$R^1$ is preferably alkyl, aryl, cycloalkyl and alkylamino. More preferably, $R^1$ is ethyl, 2-fluoroethyl, 2-hydroxyethyl, t-butyl, 4-fluorophenyl, 2,4-difluorophenyl, methyl amino and cyclopropyl. Cyclopropyl is a particularly preferred $R^1$ group. Preferred quinolone moieties also include those where $A^1$ is $C(R^7)$ and $R^1$ and $R^7$ together comprise a 6-membered heterocyclic ring containing an oxygen or sulfur atom.

$R^2$ is preferably hydrogen or halo. More preferably $R^2$ is chlorine or fluorine. Fluorine is a particularly preferred $R^2$ group.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo[2.2.1]heptane, diazabicyclo[3.2.1]octane, diazabicyclo[2.2.2]octane, thiazolidine, imidazolidine, pyrrole and thiamorpholine, as well as the following particularly preferred $R^3$ groups include piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, and 3,5-dimethylpiperazine.

Linking Moieties:

Group L, together with the $R^6$ substituent, form a variety of linking moieties between the lactam-containing structure (B) and the quinolone structure (Q) of the quinolonyl lactams. Linking moieties include the following general classes.

(1) Carbamate linking moieties, wherein L is $-X^4_t-C(=Y^2_u)-Z-Q''$; t is 1 and u is 1; $X^4$ is oxygen; $Y^2$ is oxygen; and Z is nitrogen.
(2) Dithiocarbamate linking moieties, wherein L is $-X^4_t-C(=Y^2_u)-Z-Q''$; t is 1 and u is 1; $X^4$ is sulfur; $Y^2$ is sulfur; and Z is $NR^{41}$, where $R^{41}$ is hydrogen.
(3) Urea linking moieties wherein L is $-X^4_t-C(=Y^2_u)-Z-Q''$; t is 1 and u is 1; $X^4$ is $NR^{40}$, where $R^{40}$ is hydrogen; $Y^2$ is oxygen; and Z is nitrogen.
(4) Thiourea linking moieties wherein L is $-X^4_t-C(=Y^2_u)-Z-Q''$; t is 1 and u is 1; $X^4$ is $NR^{40}$, where $R^{40}$ is hydrogen; $Y^2$ is sulfur; and Z is nitrogen.
(5) Isouronium linking moieties wherein L is $-X^4_t-C(=Y^2_u)-Z-Q''$; t is 1 and u is 1; $X^4$ is oxygen; $Y^2$ is $N^+(R^{41})(R^{42})$, where $R^{41}$ and $R^{42}$ are hydrogen; and Z is nitrogen.
(6) Isothiouronium linking moieties wherein L is $-X^4_t-C(=Y^2_u)-Z-Q''$; t is 1 and u is 1; $X^4$ is sulfur; $Y^2$ is $N^+(R^{41})(R^{42})$, where $R^{41}$ and $R^{42}$ are hydrogen; and Z is nitrogen.
(7) Guanidinium linking moieties wherein L is $-X^4_t-C(=Y^2_u)-Z-Q''$; t is 1 and u is 1; $X^4$ is $NR^{40}$, where $R^{40}$ is hydrogen; $Y^2$ is $N^+(R^{41})(R^{42})$, where $R^{41}$ and $R^{42}$ are hydrogen; and Z is nitrogen.
(8) Carbonate linking moieties wherein L is $-X^4_t-C(=Y^2_u)-Z-Q''$; t is 1 and u is 1; $X^4$ is oxygen; $Y^2$ is oxygen; and Z is oxygen.
(9) Trithiocarbonate linking moieties wherein L is $-X^4_t-C(=Y^2_u)-Z-Q''$; t is 1 and u is 1; $X^4$ is sulfur; $Y^2$ is sulfur; and Z is sulfur.
(10) Reversed carbamate linking moieties wherein L is $-X^4_t-C(=Y^2_u)-Z-Q''$; t is 1 and u is 1; $X^4$ is $NR^{40}$, $R^{40}$ is hydrogen; $Y^2$ is oxygen; and Z is oxygen.
(11) Xanthate linking moieties wherein L is $-X^4_t-C(=Y^2_u)-Z-Q''$; t is 1 and u is 1; $X^4$ is $NR^{40}$, where $R^{40}$ is hydrogen; $Y^2$ is $N^+(R^{41})(R^{42})$, where $R^{42}$ and $R^{42}$ are hydrogen; and Z is oxygen.
(12) Reversed dithiocarbamate linking moieties wherein L is $-X^4_t-C(=Y^2_u)-Z-Q''$; t is 1 and u is 1; $X^4$ is $NR^{40}$, where $R^{40}$ is hydrogen; $Y^2$ is sulfur; and Z is sulfur.
(13) Reversed isothiouronium linking moieties wherein L is $-X^4_t-C(=Y^2_u)-Z-Q''$; t is 1 and u is 1; $X^4$ is $NR^{40}$, where $R^{40}$ is hydrogen; $Y^2$ is $N^+(R^{41})(R^{42})$, where $R^{41}$ and $R^{42}$ are both hydrogen; and Z is sulfur.
(14) Amine linking moieties wherein L is $-X^3-Q''$; and $X^3$ is nitrogen.
(15) Imine linking moieties wherein L is $-X^3-Q''$; $X^3$ is nitrogen, and is linked to $R^{14}$ by a double bond.
(16) Ammonium linking moieties wherein L is $-X^3-Q''$; and $X^3$ is $N^+(R^{41})(R^{42})$.
(17) Heteroarylium linking moieties wherein L is $-X^3-Q''$; and $X^3$ is nitrogen.
(18) Ether linking moieties wherein L is $-X^2-Q''$; and $X^2$ is oxygen.
(19) Thioether, sulfoxide and sulfone linking moieties wherein L is $-X^2-Q''$; and $X^2$ is $S(O)_t$, where t=0 (thioether), t=1 (sulfoxide) or t=2 (sulfone).
(20) Ester or thioester linking moiety wherein L is $-X^4_t-C(=Y^2_u)-Z-Q''$; t is 1 and u is 1; $X^4$ is oxygen (for an ester) or sulfur (for a thioester); $Y^2$ is oxygen; and Z is nil.
(21) Amide or hydrazide linking moiety wherein $-X^4_t-C(=Y_u)-Z-Q''$; t is 1 and u is 1; $X^4$ is $N(R^{40})$, where $R^{40}$ is hydrogen (for an amide), or $X^2$ is $R^{43}-NR^{41}$ (for a hydrazide), where $R^{41}$ is hydrogen and $R^{43}$ is $NR^{41}$, and $R^{41}$ is hydrogen; $Y^2$ is oxygen; and Z is nil.

Preferred linking moieties include carbamate, dithiocarbamate, urea, thiourea, isothiouronium, amine, ammonium, ester, amide, and heteroarylium containing moieties. Particularly preferred linking moieties include carbamate, dithiocarbamate, and amine linking moieties.

The specific physical, chemical, and pharmacological properties of the quinolonyl lactams of this invention may depend upon the particular combination of the integral lactam-containing moiety, quinolone moiety and linking moiety comprising the compound. For example, selection of particular integral moieties may affect the relative susceptibility of the quinolonyl lactam to bacterial resistance mechanisms (e.g., beta-lactamase activity).

Preferred quinolonyl lactams include (for example) the following compounds.

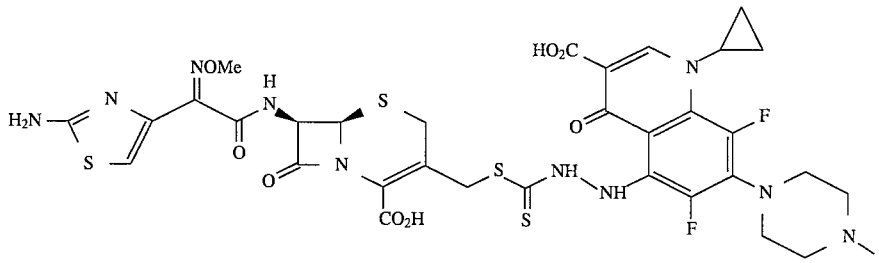

-continued
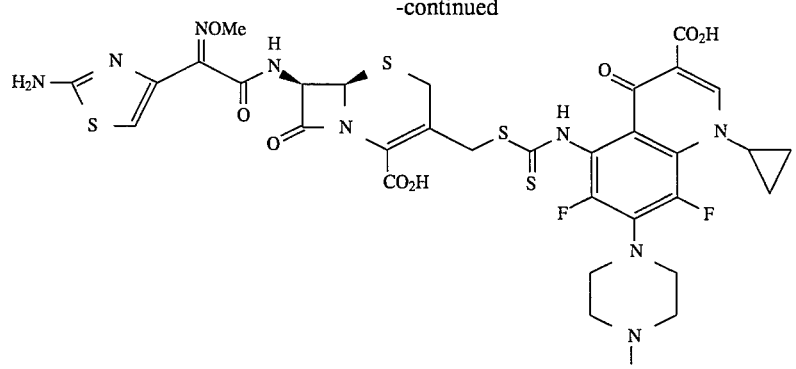
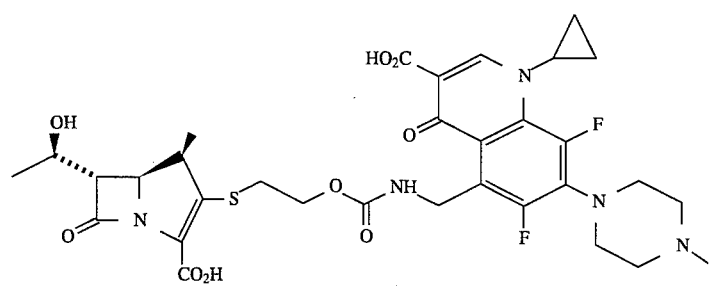
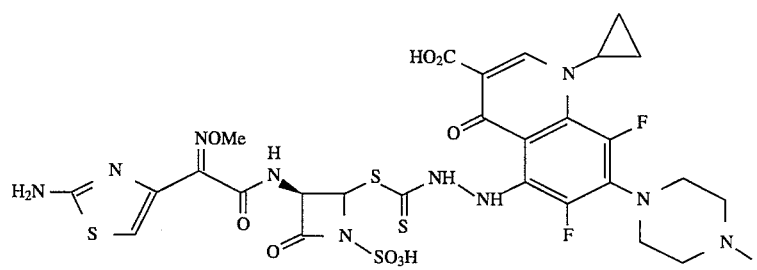
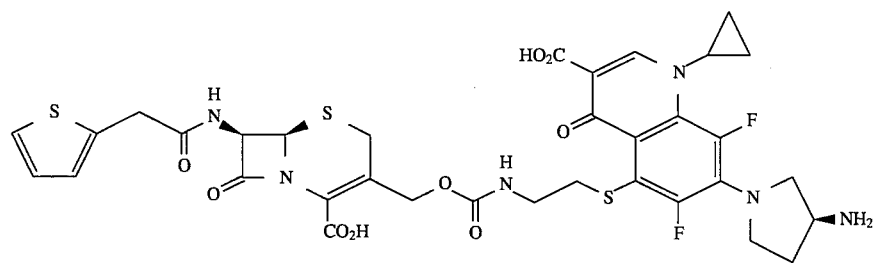
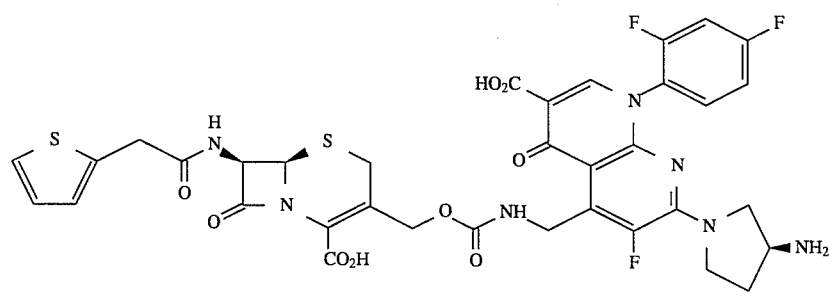

-continued
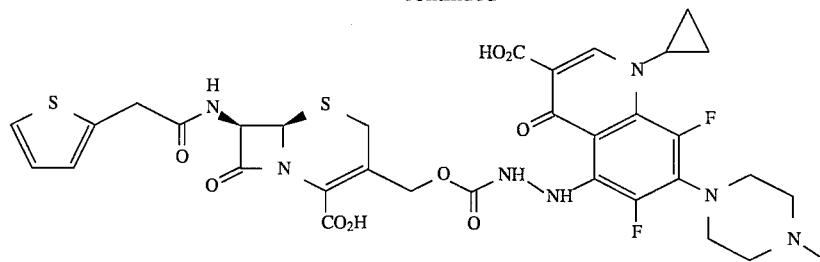
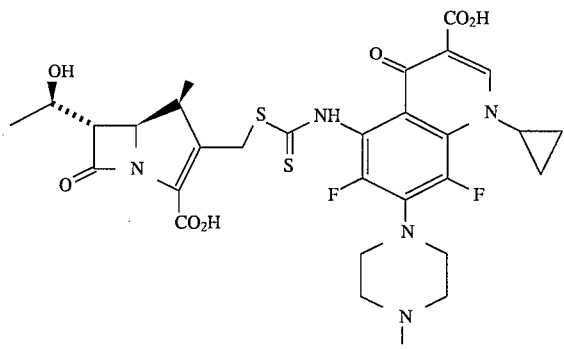
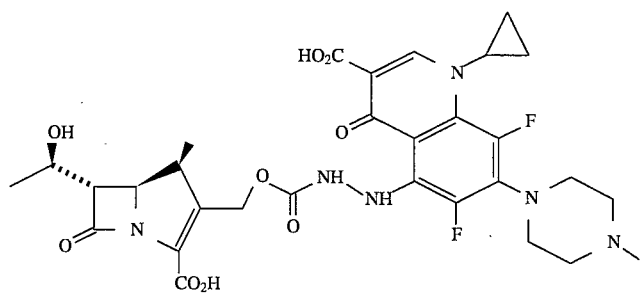
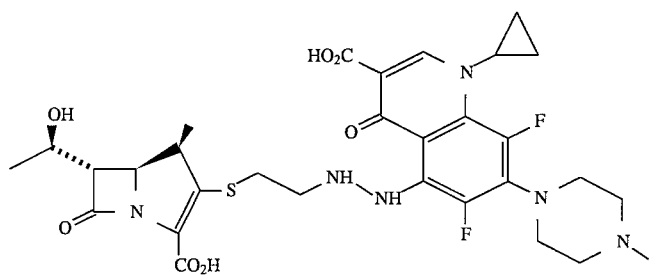
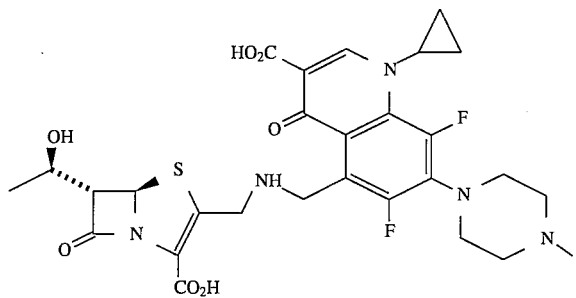

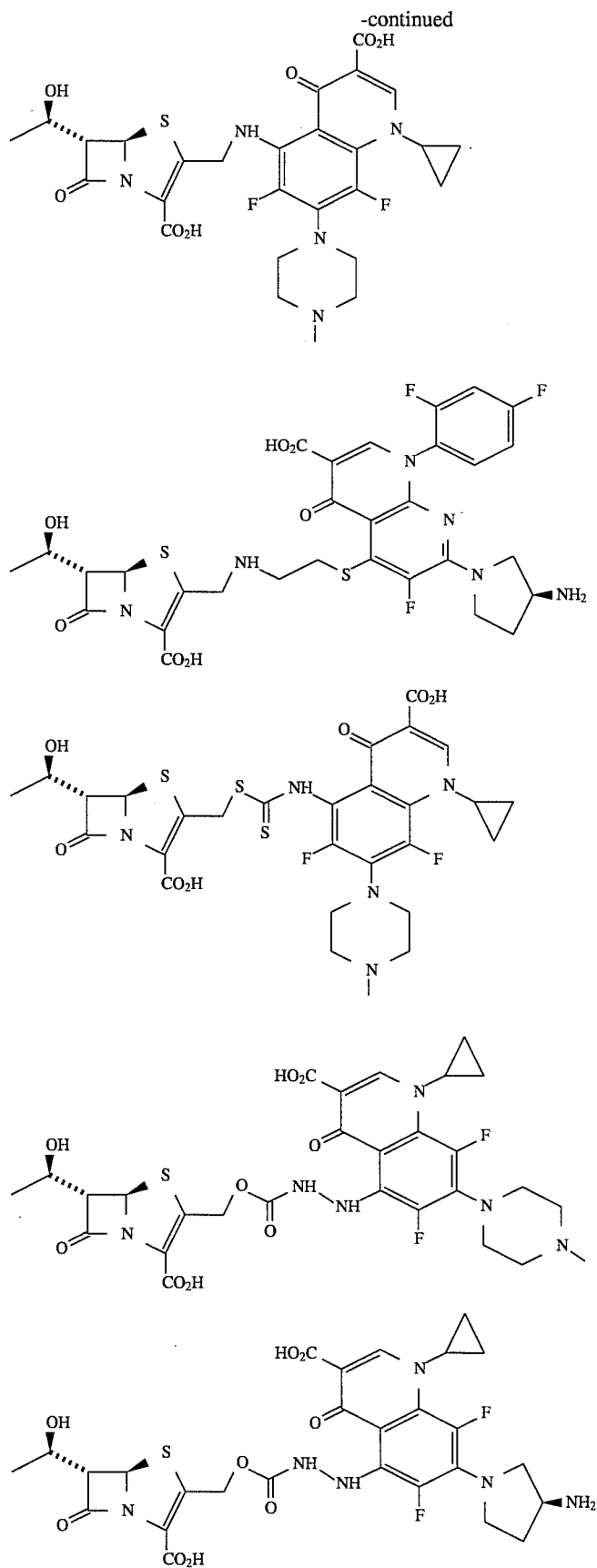

-continued

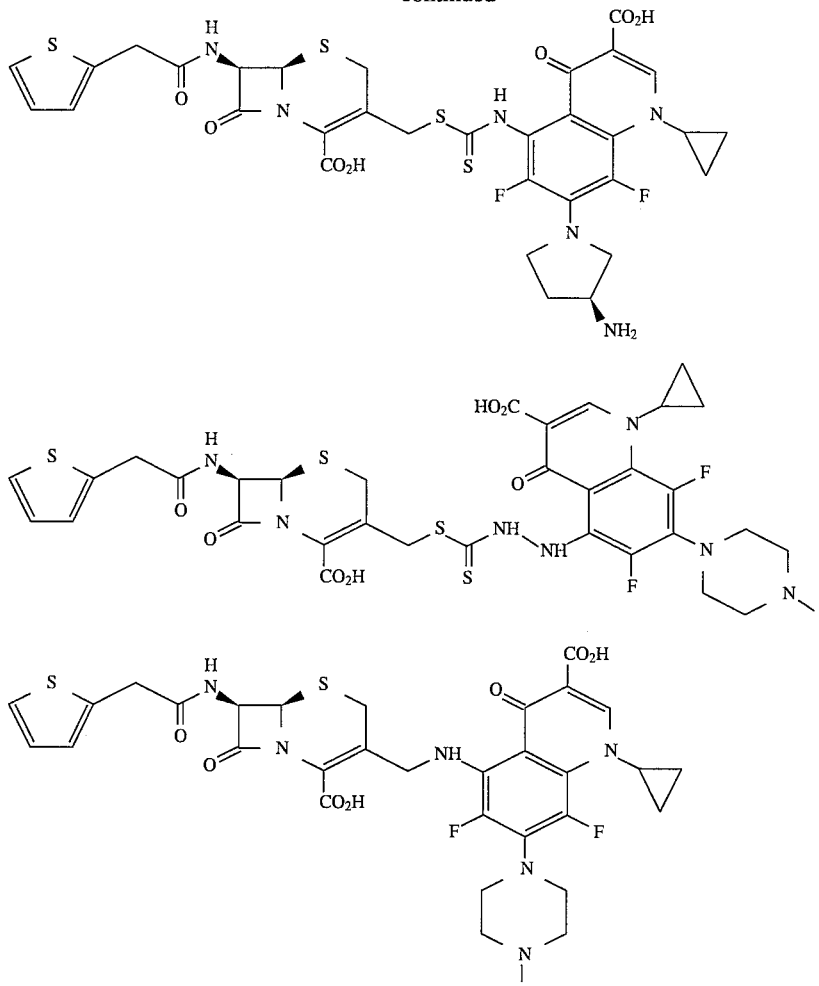

Methods of Manufacture

The quinolonyl lactams of this invention may be made using any of a variety of synthetic techniques known in the art. Manufacture of quinolonyl lactam generally involves the preparation of a lactam-containing moiety, a quinolone moiety and a procedure or set of procedures for linking the lactam-containing and quinolone moieties. Procedures for making a broad variety of lactam-containing moieties and core quinolone moieties are well known in the art. For example, procedures for preparing lactam-containing moieties are described in the following references, all incorporated by reference herein (including articles cited within these references): *Cephalosporins and Penicillins: Chemistry and Biology* (E. H. Flynn, ed, 1972) Chapters 2, 3, 4, 5, 6, 7, 15 and Appendix I; *Recent Advances in the Chemistry of β-Lactam Antibiotics* (A. G. Brown and S. M. Roberts, ed., 1985); *Topics in Antibiotic Chemistry,* Vol. 3, (Part B) and Vol. 4, (P. Sommes, ed., 1980); *Recent Advances in the Chemistry of β-lactam Antibiotics* (J. Elks, ed., 1976); *Structure-Activity Relationships Among the Semisynthetic Antibiotics* (D. Perlman, ed, 1977); Chapts. 1, 2, 3, 4; *Antibiotics, Chemotherapeutics and Antibacterial Agents for Disease Control* (M. Grayson, ed, 1982); Chemistry and Biology of β-Lactam Antibiotics, Vols 1–3 (K. B. Morin and M. Gorman, eds, 1982); 4 *Medicinal Research Reviews* 1–24 (1984); 8 *Medicinal Research Review* 393–440 (1988); 24 *Angew. Chem. Int. Ed. Engl.* 180–202 (1985); 40 *J. Antibi-*
*otics* 182–189 (1987); European Patent Publication 266,060; 42 *J. Antibiotics* 993 (1989); U.S. Pat. No. 4,742,053; 35 *Chem. Pharm. Bull.* 1903–1909 (1987); 32 *J. Med. Chem.,* 601–604 (1989); U.S. Pat. No. 4,791,106; Japanese Patent Publication 62/158291; 31 *J. Med. Chem.* 1987–1993 (1988); 30 *J. Med. Chem.,* 514–522 (1987); 28 *Tet. Let.* 285–288 (1987); 28 *Tet. Let.* 289–292 (1987); 52 *J. Org. Chem.,* 4007–4013 (1987); 40 *J. Antibiotics,* 370–384 (1987); 40 *J. Antibiotics,* 1636–1639 (1987); 37 *J. Antibiotics,* 685–688 (1984); 23 *Heterocycles,* 2255–2270; 27 *Heterocycles,* 49–55; 33 *Chem. Pharm. Bull.* 4371–4381 (1985); 28 *Tet. Let,* 5103–5106 (1987); 53 *J. Org. Chem.,* 4154–4156 (1988); 39 *J. Antibiotics,* 1351–1355 (1986); 59 *Pure and Appl. Chem.,* 467–474 (1987); 1987 *J.C.S. Chem. Comm.;* 44 *Tetrahedron,* 3231–3240 (1988); 28 *Tet. Let.,* 2883–2886, (1987); 40 *J. Antibiotics,* 1563–1571 (1987); 33 *Chem. Pharm. Bull.,* 4382–4394 (1985); 37 *J. Antibiotics,* 57–62 (1984); U.S. Pat. No. 4,631,150; 34 *Chem. Pharm. Bull.,* 999–1014 (1986); 52 *J. Org. Chem.,* 4401–4403 (1987); 39 *Tetrahedron,* 2505–2513 (1983); 38 *J. Antibiotics,* 1382–1400 (1985); European Patent Application 053, 815; 40 *J. Antibiotics,* 1563–1571 (1987); 40 *J. Antibiotics,* 1716–1732 (2987); 47 *J. Org. Chem.,* 5160–5167 (1981); U.S. Pat. No. 4,777,252; U.S. Pat. No. 4,762,922; European Patent Publication 287,734; U.S. Pat. No. 4,762,827; European Patent Publication 282,895; European Patent Publication 282,365; and U.S. Pat. No. 4,777,673.

The methods of this invention preferably use a core quinolone moiety having a non-hydrogen substituent at the 5-position (at the point of attachment of $R^6$). General procedures for preparing core quinolone moieties useful in the methods of this invention are described in the following references, all incorporated by reference herein (including articles listed within these references); 21 *Progress in Drug Research*, 9–104 (1977); 31 *J. Med. Chem.*, 503–506 (1988); 32 *J. Med. Chem.*, 1313–1318 (1989); 1987 *Liebigs Ann. Chem.*, 871–879 (1987); 14 *Drugs Exptl. Clin. Res.*, 379–383 (1988); 31 *J. Med. Chem.*, 983–991 (1988); 32 *J. Med. Chem.*, 537–542 (1989); 78 *J. Pharm. Sci.*, 585–588 (1989); 26 *J. Het. Chem.*, (1989); 24 *J. Het. Chem.*, 181–185 (1987); U.S. Pat. No. 4,599,334, 35 *Chem. Pharm. Bull.*, 2281–2285 (1987); 29 *J. Med. Chem.*, 2363–2369 (1986); 31 *J. Med. Chem.*, 991–1001 (1988); 25 *J. Het. Chem.*, 479–485 (1988); European Patent Publication 266,576; European Patent Publication 251,308, 36 *Chem. Pharm. Bull.*, 1223–1228 (1988); European Patent Publication 227, 088; European Patent Publication 227,039; European Patent Publication 228,661; 31 *J. Med. Chem.*, 1586–1590 (1988); 31 *J. Med. Chem.*, 1598–1611 (1988); and 23 *J. Med. Chem.*, 1358–1363 (1980);

A general procedure for preparing 5-substituted quinolones useful in the methods of this invention includes treating an appropriate core quinolone moiety, having a 5-fluoro substituent, with various nucleophiles (for example, amines, thiols, azide, and cyanide) in an inert polar solvent, such as dimethyl formamide (DMF) or dimethyl sulfoxide (DMSO). Further elaboration of the $R^6$ group, to produce quinolone moieties useful in this invention, may be performed by known procedures for protecting group removal, functional group modification and/or (for example) interconversion or homologation.

Preparation of core quinolone moieties having a non-hydrogen substituent at the 5-position are (for example) described in the following documents, all of which are incorporated by reference herein: 32 *J. Med. Chem.* 1313 (1989); European Patent Publication 342,649 (1989); European Patent Publication 309,789 (1988); World Patent Publication 89/06649 (1989); European Patent Publication 310, 917 (1989); European Patent Publication 312,085 (1989); European Patent Publication 304,087 (1989); European Patent Publication 305,744 (1989); European Patent Publication 306,860 (1989); European Patent Publication 287,951 (1988); German Offenlegungsschrift 3,711,193 (1983); European Patent Publication 265,230 (1988); European Patent Publication 247,464 (1987); European Patent Publication 255,908 (1988); European Patent Publication 242,789 (1987); European Patent Publication 230,053 (1987); 31 *J. Med. Chem.* 503 (1988); European Patent Publication 230, 946 (1987); European Patent Publication 230,295 (1987); European Patent Publication 221,463 (1987); European Patent Publication 226,961 (1987); European Patent Publication 172,651 (1986); and European Patent Publication 115,334 (1984).

Procedures for linking the lactam-containing moiety and quinolone moieties may vary according to the type of linking group desired. For example, the quinolonyl lactams having a carbamate linking moiety may be made by the following general reaction sequence:

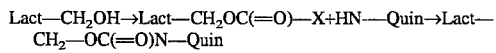

where X is a reactive leaving group (such as alkoxy, halo, or N-heteroaryl), "Lact" represents an appropriately protected lactam-containing structure (such as a penem, carbapenem, cephem, monocyclic beta-lactam, oxacephem, or carbacephem) and "Quin" represents an appropriately protected quinolone. The sequence can be envisioned as formation of the intermediate lactam carbonate derivative, followed by acylation of a quinolone amino functionality to form a carbamate coupled conjugate of the lactam and quinolone.

Alternatively, "reversed" dithiocarbamate conjugates can be prepared by the following sequence.

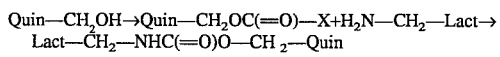

where X is a reactive leaving group (such as alkoxy, halo, or N-heteroaryl), "Lact" represents an appropriately protected lactam-containing structure (such as a penem, carbapenem, cephem, oxacephem, or carbacephem) and "Quin" represents an appropriately protected quinolone. The sequence can be envisioned as formation of the intermediate quinolone carbonate derivative, followed by acylation of a lactam amino functionality to form a carbamate coupled conjugate of the lactam and quinolone.

Lactam-Quinolones having a dithiocarbamate linking moiety may be made by the following general reaction sequence:

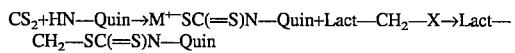

where X is a reactive leaving group (such as halo, a sulfonate ester, acetate, thiobenzoate or other activated hydroxyl functionality), "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate quinolone dithiocarbamate salt, followed by nucleophilic displacement of the lactam X substituent to form a dithiocarbamate coupled conjugate of the lactam and quinolone.

Alternatively, "reversed" dithiocarbamate conjugates can be prepared by the following sequence.

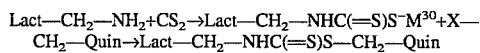

where X is a reactive leaving group (such as halo, a sulfonate ester, or other activated hydroxyl functionality), "Lact" represents an appropriately protected lactam-containing structure (such as a penem, carbapenem, cephem, oxacephem, or carbacephem), and "Quin" represents an appropriately protected quinolone. The sequence can be envisioned as formation of the intermediate lactam dithiocarbamate salt, followed by nucleophilic displacement of the suitable quinolone X substituent to form a "reversed" dithiocarbamate coupled conjugate of the lactam and quinolone. Quinolonyl lactams having a thiourea or urea linking moiety may be made by the following general reaction sequence:

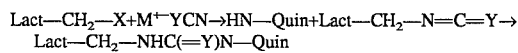

(thiourea: Y is sulfur; urea: Y is oxygen)

where X is a reactive leaving group (such as halo, a sulfonate ester, dichloroacetate, thiobenzoate or other activated hydroxyl functionality), and Y is either O or S. "Lact" represents an appropriately protected lactam-containing structure (such as a penem, carbapenem, cephem, monocyclic beta-lactam, oxacephem, or carbacephem), and "Quin"

represents an appropriately protected quinolone. The sequence can be envisioned as formation of the intermediate lactam isothiocyanate (Y=S) or isocyanate (Y=O), followed by reaction with the quinolone amino substituent to form a thiourea (Y=S) or urea (Y=O) coupled conjugate of the lactam and quinolone.

Alternatively, the thiourea or urea conjugates can be prepared by the following sequence.

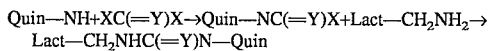

(thiourea: Y is sulfur; urea: Y is oxygen)

where X is a reactive leaving group such as halo, N-heteroaryl or activated hydroxyl functionality, and Y is either S or O. "Lact" represents an appropriately protected lactam-containing structure (such as penem, carbapenem, cephem, monocyclic beta-lactam, oxacephem, or carbacephem), and "Quin" represents an appropriately protected quinolone. The sequence can be envisioned as formation of the intermediate quinolone activated thio carbamate (Y=S) or carbamate (Y=O), followed by reaction with the lactam amino substituent to form a thiourea (Y=S) or urea (Y=O) coupled conjugate of the lactam and quinolone.

Quinolonyl lactams having an imine, amine or ammonium linking moiety may be made by the following general reaction sequence:

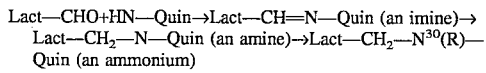

"Lact" represents an appropriately protected lactam-containing structure (such as a penem, carbapenem, cephem, oxacephem, or carbacephem), and "Quin" represents an appropriately protected quinolone. The sequence can be envisioned as the condensation of the quinolone amine with the lactam aldehyde to form the imine coupled quinolonyl lactam conjugate. Reduction of the imine yields the corresponding amine coupled lactam-quinolone conjugate. Alkylation yields the corresponding quaternary ammonium-coupled quinolonyl lactam conjugate.

Alternatively, the quaternary ammonium and amine (R is H) conjugates can be prepared by the following general sequence.

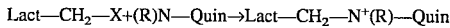

where X is a reactive leaving group (such as halo, a sulfonate ester, or other activated hydroxyl functionality, etc.) This sequence can be envisioned as an alkylation of a quinolone amino group with the lactam starting material to obtain the amine or quaternary ammonium coupled conjugate between the lactam and quinolone.

Quinolonyl lactams having an amide linking moiety may be made by the following general reaction sequence:

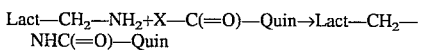

where X is a reactive leaving group (such as halo, an HOBt ester, mixed anhydride or other activated carboxyl functionality), "Lact" represents an appropriately protected lactam-containing structure (such as a penem, carbapenem, cephem, oxacephem, or carbacephem),, and "Quin" represents an appropriately protected quinolone. The reaction can be envisioned as an acylation of the lactam amino substituent with the activated quinolone carboxyl group, to form an amide coupled conjugate of the lactam and quinolone.

Alternatively, "reversed" amide conjungates can be prepared by the following sequence.

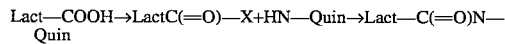

where X is a reactive leaving group (such as halo, an HOBT ester, mixed anhydride or another activated carboxyl functionality), "Lact" represents an appropriately protected lactam-containing structure (such as a penem, carbapenem, cephem, oxacephem or carbacephem), and "Quin" represents an appropriately protected quinolone. The reaction can be envisioned as an acylation of the quinolone amino substituent with the activated lactam carboxyl group to form a 37 reversed" amide coupled conjungate of the lactam and quinolone.

Quinolonyl lactams having a guanidinium linking moiety may be made by the following general reaction sequence:

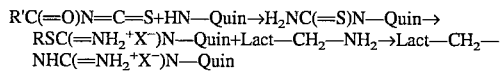

where "Lact" represents an appropriately protected lactam-containing structure (such as penem, carbapenem, cephem, oxacephem, or carbacephem) and "Quin" represents an appropriately protected quinolone. The sequence can be envisioned as formation of the intermediate quinolone isothiouronium salt, followed by reaction with the lactam amino substituent to form a guanidinium coupled conjugate of the lactam and quinolone.

Quinolonyl lactams having a heteroarylium linking moiety may be made by the following general reaction sequence:

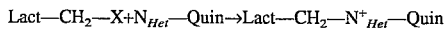

where X is a reactive leaving group (such as halo, a sulfonate ester, acetate, thiobenzoate or other activated hydroxyl functionality), "Lact" represents an appropriately protected lactam-containing structure {such as a penem, carbapenem, cephem, monocyclic beta-lactam, oxacephem, or carbacephem) and "Quin" represents an appropriately protected quinolone that contains a heteroaromatic nitrogen-containing substituent (for example, pyridine). The sequence can be envisioned as an alkylation of the quinolone heteroaromatic nitrogen containing substituent by the lactam to form the pyridinium-type conjugate.

Quinolonyl lactams having a xanthate linking moiety may be made by the following general reaction sequence:

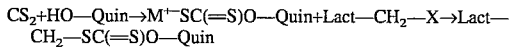

where X is a reactive leaving group (such as halo, a sulfonate ester, acetate, thiobenzoate or other activated hydroxyl functionality), "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as formation of the intermediate quinolone xanthate salt, followed by nucleophilic displacement of the lactam X substituent to form a xanthate coupled conjugate of the lactam and quinolone.

Quinolonyl lactams having a thioether, sulfoxide or sulfone linking moiety may be made by the following general reaction sequence:

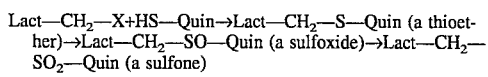

Lact—CH$_2$—X+HS—Quin→Lact—CH$_2$—S—Quin (a thioether)→Lact—CH$_2$—SO—Quin (a sulfoxide)→Lact—CH$_2$—SO$_2$—Quin (a sulfone)

where X is a reactive leaving group (such as halo, a sulfonate ester, acetate, thiobenzoate or other activated hydroxyl functionality, etc.). "Lact" represents an appropriately protected lactam-containing structure (such as a penem, carbapenem, cephem, monocyclic beta-lactam, oxacephem, or carbacephem), and "Quin" represents an appropriately protected quinolone. The sequence can be envisioned as nucleophilic displacement of the lactam X group with a thio-containing quinolone to form the thioether coupled conjugate of the lactam and the quinolone. Oxidation of the thioether yields the corresponding sulfoxide conjugate. Further oxidation produces the sulfone quinolonyl lactam conjugate.

Quinolonyl lactams having a vinyl-thioether linking moiety may be made by the following general reaction sequence:

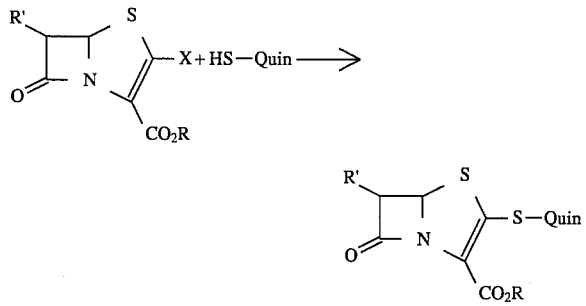

where X is a reactive vinylic leaving group (such as halo, sulfonate ester, phosphate ester or other activated enolic functionality, etc.) The lactam-containing structure may be a penem, as represented above, or more may be another appropriately protected lactam-containing structure (such as carbapenem, cephem, oxacephem, or carbacephem), and "Quin" represents an appropriately protected quinolone possessing a thiol substituent. The sequence can be envisioned as the displacement of the vinylic lactam X substituent to form the corresponding vinyl-thioether coupled conjugate of the lactam and quinolone.

Quinolonyl lactams having an isothiouronium linking group may be made by the following general reaction sequence:

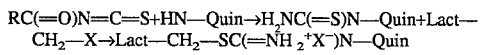

RC(=O)N=C=S+HN—Quin→H$_2$NC(=S)N—Quin+Lact—CH$_2$—X→Lact—CH$_2$—SC(=NH$_2{}^+$X$^-$)N—Quin where X is a reactive leaving group (such as halo, a sulfonate ester, acetate, thiobenzoate or other activated hydroxyl functionality). Lact represents an appropriately protected lactam-containing structure (such as a penem, carbapenem, cephem, monocyclic beta-lactam, oxacephem, or carbacephem, and "Quin" represents an appropriately protected quinolone. The sequence can be envisioned as formation of the intermediate quinolone thiourea, followed by nucleophilic displacement of the lactam X substituent to form a isothiouronium coupled conjugate of the lactam and quinolone.

In the reaction sequences described herein, certain functional groups contained in the Lact and Quin structures, (such as carboxyl, hydroxyl, and amino groups) may need to be blocked in order to prevent undesired competing side reactions from occurring with X. Suitable protecting groups for carboxyl substituents include esters. Protecting groups for hydroxyl substituents include ethers, esters, and carbonates; and protecting groups for amino substituents include carbamates, and amides. If various protecting groups are employed, then appropriate deprotecting chemistry, that will not decompose the coupled conjugate, may be required to obtain antibacterially active products.

Compositions

The compositions of this invention comprise:

(a) a safe and effective amount of a quinolonyl lactam; and (b) a pharmaceutically-acceptable carrier.

A "safe and effective amount" of a quinolonyl lactam is an amount that is effective, to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the quinolonyl lactam therein, and the dosage regimen desired for the composition.

The compositions of this invention are preferably provided in unit dosage form. As used herein, a "unit dosage form" is a composition of this invention containing an amount of a quinolonyl lactam that is suitable for administration to a human or lower animal subject, in a single dose, according to good medical practice. These compositions preferably contain from about 30 mg to about 20,000 mg, more preferably from about 50 mg (milligrams) to about 7000 mg, more preferably from about 500 mg to about 3500 mg, of a quinolonyl lactam.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolonyl lactam. The amount of carrier employed in conjunction with the quinolonyl lactam is sufficient to provide a practical quantity of material for administration per unit dose of the quinolonyl lactam. Techniques and compositions for making dosage forms useful in the methods of this invention are described in the following references, all incorporated by reference herein: 7 *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight by the total composition.

Various oral dosage forms can be used, including such solid forms as tablets, capsules, granules and bulk powders. These oral forms comprise a safe and effective amount, usually at least about 5%, and preferably from about 25% to about 50%, of the quinolonyl lactam. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolonyl lactam. Suitable carriers for topical administration preferably remain in place on the skin as a continuous film, and resist being removed by perspiration or immersion in water. Generally, the carrier is organic in nature and capable of having dispersed or dissolved therein the quinolonyl lactam. The carrier may include pharmaceutically-acceptable emollients, emulsifiers, thickening agents, and solvents.

Methods of Administration

This invention also provides methods of treating or preventing an infectious disorder in a human or other animal subject, by administering a safe and effective amount of a quinolonyl lactam to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients (such as patients receiving cancer chemotherapy, or organ transplant patients).

The quinolonyl lactams and compositions of this invention can be administered topically or systemically. Systemic application includes any method of introducing the quinolonyl lactam into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific quinolonyl lactam used, the resistance pattern of the infecting organism to the quinolonyl lactam used, the ability of the quinolonyl lactam to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 75 mg to about 30,000 mg, more preferably from about 100 mg to about 20,000 mg, more preferably from about 500 mg to about 3500 mg, of quinolonyl lactam are administered per day. Treatment regimens preferably extend from about 1 to about 56 days, preferably from about 7 to about 28 days, in duration. Prophylactic regimens (such as avoidance of opportunistic infections in immunocompromised patients) may extend 6 months, or longer, according to good medical practice.

A preferred method of parenteral administration is through intramuscular injection. As is known and practiced in the art, all formulations for parenteral administration must be sterile. For mammals, especially humans, (assuming an approximate body weight of 70 kilograms) individual doses of from about 100 mg to about 7000 mg, preferably from about 500 mg to about 3500 mg, are acceptable.

A preferred method of systemic administration is oral. Individual doses of from about 100 mg to about 2500 mg, preferably from about 250 mg to about 1000 mg are preferred.

Topical administration can be used to deliver the quinolonyl lactam systemically, or to treat a local infection. The amounts of quinolonyl lactam to be topically administered depends upon such factors as skin sensitivity, type and location of the tissue to be treated, the composition and carrier (if any) to be administered, the particular quinolonyl lactam to be administered, as well as the particular disorder to be treated and the extent to which systemic (as distinguished from local) effects are desired.

The following non-limiting examples illustrate the compounds, compositions, processes, and uses of the present invention.

EXAMPLE 1

[6R-[6α,7β]]-3-[[[[2-[3-Carboxy-1-cyclopropyl-6,8-difluoro-1,4 -dihydro-7-(4-methyl-1-piperazinyl)-4-oxo-5-quinolinyl]-1-hydrazino]thioxomethyl]thio]methyl]-8-oxo-7-(2-thienylacetyl)amino-5-thia-1-azabicyclo[4.2.0] oct-2-ene-2-carboxylic acid disodium salt is made according to the following general procedure.

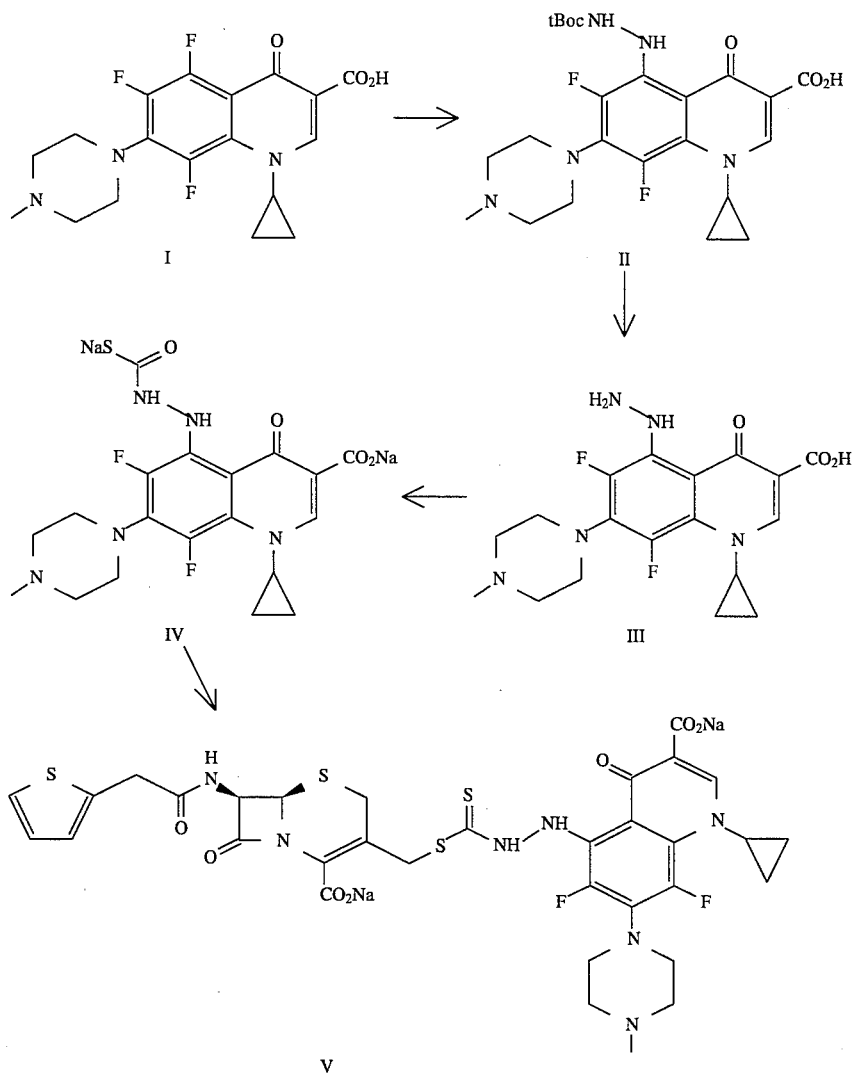

To a mixture of 11.4 gm 1-cyclopropyl-5,6,8-trifluoro-1,4-dihydro-7-(4-methyl-1-piperazinyl)- 4-oxo-quinoline-3-carboxylic acid (Compound I, prepared according to D. B. Moran, et al., 32 *J. Med. Chem.* 1313–1318 (1989)) and 7.25 gm t-butyl carbazate in 70 ml dimethylsulfoxide at about 35° C. with stirring under nitrogen is added 14.1 ml of triethylamine slowly. The reaction is heated at about 90°–95° C. for 5 hr and then cooled. Acetonitrile is added and allowed to stir overnight. The resulting precipitate is collected and dried to give 11.34 gm of Compound II.

Compound II (10.5 gm) is stirred in approximately 50 ml trifluoroacetic acid for 1 hr at room temperature. The solvent is evaporated, the crude residue dissolved in 1N HCl and precipitated by the addition of acetone. The solid is collected and air-dried to yield 6.05 gm of Compound III as the dihydrochloride salt.

Compound III (4.65 gm) is suspended in approximately 10 ml water and 10 ml of 4N NaOH is added, followed by 1.7 gm carbon disulfide. The reaction is stirred at room temperature for 4 hr, then the addition of acetone precipitates the product which is collected by filtration. Trituration of this material in acetone then gives 3.1 gm Compound IV.

To a solution of 2.6 gm Compound IV in 20 ml water is added a pH 8 (adjusted with sodium carbonate) solution of cephalothin sodium salt (2.4 gm). The solution is heated at about 45° C. for about 15 hr, then concentrated in vacuo and the product is isolated by preparative reverse phase chromatography (C18, acetonitrile/water) to yield 1.49 gm of Compound V.

EXAMPLE 2

[5R-[5α,6α]]-3-[[[[[2-[[3-Carboxy-1-cyclopropyl-6,8-difluoro- 1,4-dihydro-7-(4-methyl-1-piperazinyl)-4-oxo-5-quinolinyl]thio]-1-ethyl]amino]carbonyl]oxy]methyl]-6-[(R)-1-hydroxyethyl]-7-oxo-4-thia-1-azabicyclo[3.2.0] hept-2-ene-2 -carboxylic acid disodium salt is made according to the following general procedure.

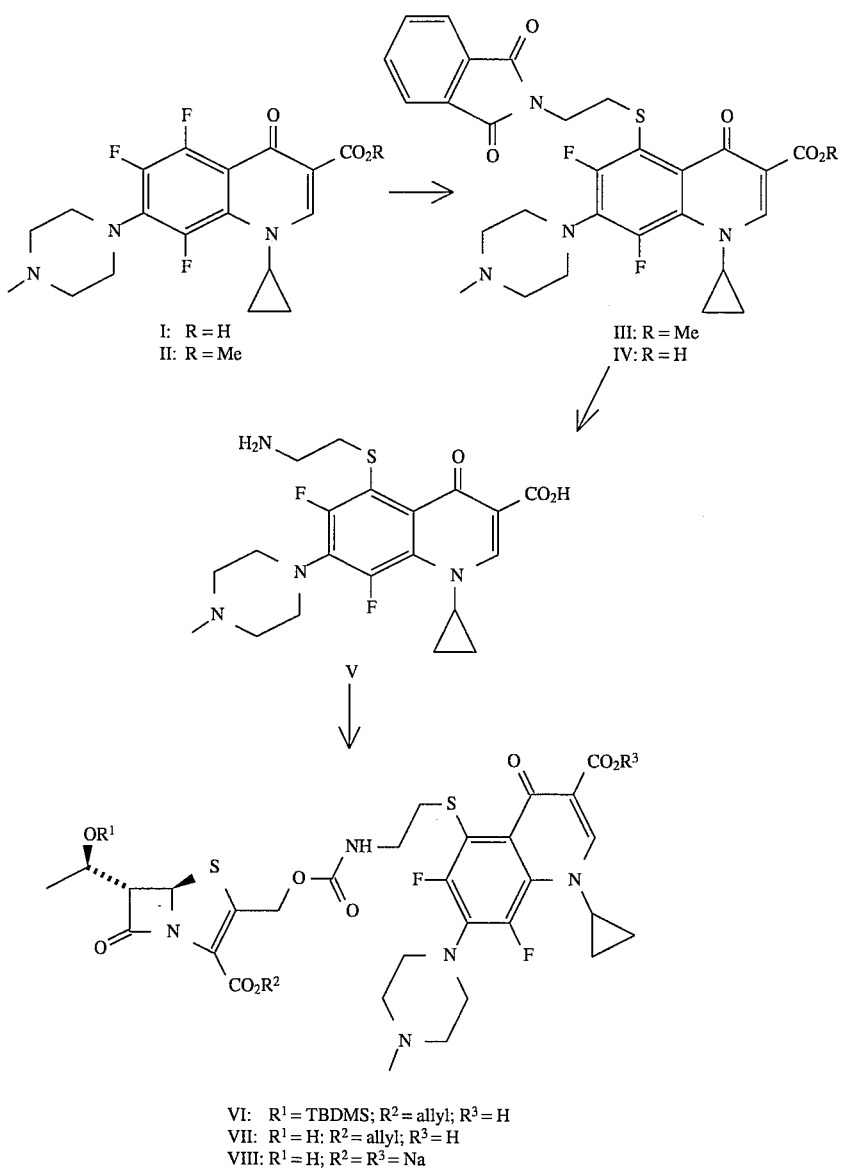

VI: R¹ = TBDMS; R² = allyl; R³ = H
VII: R¹ = H; R² = allyl; R³ = H
VIII: R¹ = H; R² = R³ = Na To 23.0 gm of 1-cyclopropyl-5,6,8-trifluoro-1,4-dihydro-7-(4-methyl-1-piperazinyl)-4 -oxo-quinoline-3-carboxylic acid (Compound I, prepared according to D. B. Moran, et al., 32 *J. Med. Chem.* 1313–1318 (1989)) in approximately 600 ml anhydrous methanol is added 14.5 gm thionyl chloride dropwise at about 5°–10° C. The reaction mixture is then refluxed for 18 hr, cooled, and concentrated in vacuo. The residue is taken up in chloroform and extracted with 10% aqueous sodium carbonate. The organic layer is dried over sodium sulfate and concentrated. The crude solid is recrystallized from acetonitrile to yield 15.1 gm Compound II.

To 11.8 gm of Compound II and 6.83 gm of N-(2-mercaptoethyl)phthalimide in 400 ml dry 50% THF/DMF is added 1.45 gm NaH (60% in mineral oil) portionwise at about 0°–5° C. with stirring under nitrogen. The reaction is stirred for 2 hr and poured into cold saturated brine. The aqueous layer is extracted with chloroform. The combined organic layers are dried over sodium sulfate and concentrated in vacuo. The residue is triturated in acetone/hexanes and collected. The solid is then chromatographed on silica gel (ethyl acetate/methylene chloride) to yield 7.15 gm Compound III.

Compound III (7.1 gm) in a mixture of about 250 ml methanol and 250 ml 6N HCl is refluxed for 4 hr. The reaction is cooled and concentrated to dryness. The crude product is dissolved in minimal aqueous DMF and is precipitated by neutralization with 10% aqueous sodium bicarbonate solution. The solid is collected and air-dried to yield 4.71 gm of Compound IV.

To 4.54 gm of Compound IV in 200 ml 50% DMF/absolute ethanol is added 8 ml of 1N hydrazine hydrate in absolute ethanol. The mixture is refluxed for 6 hr and evaporated to dryness. The residue is treated with 25 ml 2N HCl at about 50° C. for 20 min, then cooled at room temperature for approximately 1 hr. The mixture is filtered and the filtrate is evaporated. The crude product is triturated in acetonitrile, collected and redissolved in water. A 10% sodium bicarbonate solution is added to precipate Compound V, which is filtered and dried yielding 2.52 gm.

To a solution of 2.27 gm of 3-hydroxymethyl-6-[1-[(1,1-dimethylethyl)dimethylsilyloxy]ethyl]-7 -oxo-4-thia-1-azabicyclo[3.2.0]hept-2-ene-2-carboxylic acid, allyl ester (prepared according to C. Battistini, et al., U.S. Pat. No. 4,631,150) in 35 ml dry THF at about 0° C. is added 1,2,2,2-tetrachloroethyl chloroformate (0.88 ml) followed by the dropwise addition of 0.54 ml pyridine Over 5 min. The mixture is stirred at about 0° C. for 60 min and poured into a mixture of Compound V (2.19 gm) in 23 ml water containing 2.6 gm sodium bicarbonate. The resulting mixture is then stirred for 70 min, cooled in an ice bath and diluted with 200 ml of cold 0.2N HCl. The solution is evaporated to dryness and the residue is triturated with ether. The solid is collected and subsequently purified by flash chromatography (silica gel, isopropanol/chloroform/acetic acid) to yield 0.60 gm Compound VI.

To a solution of 0.51 gm Compound VI in 15 ml THF containing 0.33 ml glacial acetic acid at room temperature is added 0.55 gm tetrabutylammonium fluoride trihydrate. The mixture is stirred for 24 hr, the solvent is removed in vacuo, and the crude product is purified by flash chromatography (silica gel, chloroform/methanol/acetic acid) to yield 201 mg Compound VII.

To 186 mg of compound VII in 20 ml DMF containing 4 mg bis(triphenylphosphine)palladium(II) chloride and 25 ml acetic acid is added 0.15 ml tributyltin hydride at about 0° C. The reaction is stirred under nitrogen for 30 min and concentrated to 1–2 ml. The residue is diluted with ether to precipitate the crude product. The solvent is decanted and the residue is suspended in 3 ml acetone at about 0° C. A cold solution of 42 mg sodium bicarbonate in 1.5 ml water is added. The resultant solution is then diluted with acetone and the precipitated product is collected by filtration, yielding 141 mg of Compound VIII after air-drying.

EXAMPLE 3

An antimicrobial composition for parenteral administration, according to this invention, is made comprising:

| Component | Amount |
| --- | --- |
| compound of Example 1 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated.

EXAMPLE 4

An enteric coated antimicrobial composition for oral administration, according to this invention, is made comprising the following core tablet:

| Component | Amount (mg) |
| --- | --- |
| compound of Example 2 | 350.0 |
| starch | 30.0 |
| magnesium stearate | 5.0 |
| microcrystalline cellulose | 100.0 |
| colloidal silicon dioxide | 2.5 |
| povidone | 12.5 |

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 14 days. Symptoms of the disease then subside, indicating substantial eradication of the pathogen.

What is claimed is:

1. A compound of the formula

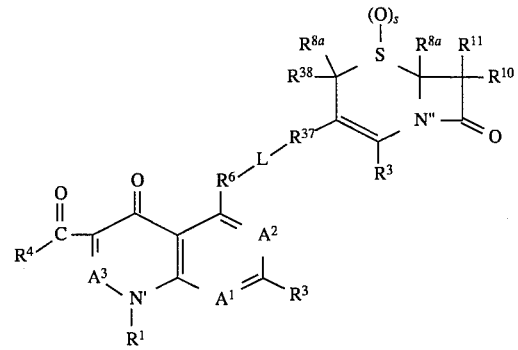

wherein
(A) (1) $A^1$ is $C(R^7)$; where
   (i) $R^7$ is hydrogen, hydroxy, alkoxy, nitro, cyano, halogen, $C_1$–$C_8$ alkyl, or $N(R^8)(R^9)$, and
   (ii) $R^8$ and $R^9$ are, independently, $R^{8a}$ where $R^{8a}$ is hydrogen, $C_1$–$C_8$ alkyl, $C_2$–$C_8$ alkenyl, 3–9 atom monocyclic or 7–17 atom polycyclic carbocycle, or 3–9 atom monocyclic or 7–17 atom polycyclic heterocycle; or $R^8$ and $R^9$ together form [comprise]a 3–9 atom monocyclic or 7–17 atom polycyclic heterocycle including the nitrogen to which they are bonded; wherein said heterocycles have one or more heteroatoms selected from O, S, or N;

(2) $A^2$ is $C(R^2)$; where $R^2$ is hydrogen or halogen;

(3) $A^3$ is $C(R^5)$; where $R^5$ is hydrogen;

(4) $R^1$ is hydrogen, $C_1$–$C_8$ alkyl, a 3–9 atom monocyclic or 7–17 atom polycyclic carbocycle, a 3–9 atom monocyclic or 7–17 atom polycyclic heterocycle, alkoxy, hydroxy, $C_2$–$C_8$ alkenyl, arylalkyl, or $N(R^8)(R^9)$; wherein said heterocycle has one or more heteroatoms selected from O, S, or N; and wherein said arylalkyl is a $C_1$–$C_8$ alkyl substituted with an aryl group;

(5) $R^3$ is hydrogen, halogen, $C_1$–$C_8$ alkyl, a 3–9 atom monocyclic or 7–17 atom polycyclic carbocycle, or a 3-9 atom monocyclic or 7–17 atom polycyclic heterocycle; wherein said heterocycle has one or more heteroatoms selected from O, S, or N;

(6) $R^4$ is hydroxy; and (7) $R^6$ is $R^{15}$ or $R^{16}X$; where $R^{15}$ is a substituent moiety of L and is nil, $C_1$–$C_8$ alkyl, a 3–8 atom heteroalkyl having one or two heteroatoms selected from O, S, or N or $C_2$–$C_8$ alkenyl; $R^{16}$ is a substituent moiety of L and is $C_1$–$C_8$ alkyl, $C_2$–$C_8$ alkenyl, a 3–9 atom monocyclic or 7–17 atom polycyclic carbocycle or a 3–9 atom monocyclic or 7–17 atom polycyclic heterocycle; wherein said heterocycle has one or more heteroatoms selected from O, S, or N; and X is $C_1$–$C_8$ alkyl, a 3–8 atom heteroalkyl having one or two heteroatoms selected from O, S, or N; $C_2$–$C_8$ alkenyl, oxygen, sulfur, or NH;

(B) except that (1) $R^1$ and $R^7$ may together form a 3–9 atom monocyclic or 7–17 atom polycyclic heterocycle including N' and $A^1$ wherein said heterocycle has one or more heteroatoms selected from O, S, or N;

(2) $R^2$ and $R^3$ may together form —O—$(C_2)_n$—O—, where n is an integer from 1 to 4;

(3) $R^4$ and $R^5$ may together form a 3–9 atom monocyclic or 7–17 atom polycyclic heterocycle including the carbon atoms to which $R^4$ and $R^5$ are bonded and the carbon atom to which said carbon atoms are bonded; and (4) $R^1$ and $R^5$ may together form a 3–9 atom monocyclic or 7–17 atom polycyclic heterocycle including N' and the adjacent carbon to which $R^5$ is bonded wherein said heterocycle has one or more heteroatoms selected from O, S, or N;

(C) $R^{10}$ is hydrogen, halogen, $C_1$–$C_8$ alkyl, $C_2$–$C_8$ alkenyl, a 3–8 atom heteroalkyl having one or two heteroatoms selected from O, S, or N, a 3–9 atom monocyclic or 7–17 atom polycyclic carbocycle, a 3–9 atom monocyclic or 7–17 atom polycyclic heterocycle wherein said heterocycle has one or more heteroatoms selected from O, S, or N, $R^{8a}$—O—, $R^{8a}$CH=N—, $(R^8)(R^9)$N—, $R^{17}$—C(=CHR$^{20}$)—C(=O)NH—, $R^{17}$—C(=NO—R$^{19}$)—C(=O)NH—, or $R^{18}$—(CH$_2$)$_m$—C(=O)NH—; where (1) m is an integer from 0 to 9;

(2) $R^{17}$ is hydrogen, $C_1$–$C_8$ alkyl, $C_2$–$C_8$ alkenyl, a 3–8 atom heteroalkyl having one or two heteroatoms selected from O, S, or N, a 3–8 atom heteroalkenyl having one or two heteroatoms selected from O, S, or N, a 3–9 atom monocyclic or 7–17 atom polycyclic carbocycle, or a 3–9 atom monocyclic or 7–17 atom polycyclic heterocycle; wherein said heterocycle has one or more heteroatoms selected from O, S, or N;

(3) $R^{18}$ is $R^{17}$, —$Y^1$, or —CH($Y^2$)($R^{17}$);

(4) $R^{19}$ is $R^{17}$, arylalkyl, heteroarylalkyl, —C($R^{22}$)($R^{23}$)COOH, —C(=O)O—$R^{17}$, or —C(=O)NH—$R^{17}$, where $R^{22}$ and $R^{23}$ are, independently, $R^{17}$ or together form a 3–9 atom monocyclic or 7–17 atom polycyclic carbocycle or a 3–9 atom monocyclic or 7–17 atom polycyclic heterocycle including the carbon atom to which $R^{22}$ and $R^{23}$ are bonded; wherein said heterocycle has one or more heteroatoms selected from O, S, or N; and wherein said arylalkyl is a $C_1$–$C_8$ alkyl substituted with an aryl group and wherein said heteroalkyl is a $C_1$–$C_8$ alkyl substituted with an aryl group substituted with a heteroatom selected from O, S, or N;

(5) $R^{20}$ is $R^{19}$, halogen, —$Y^1$, or —CH($Y^2$)($R^{17}$);

(6) $Y^1$ is —C(=O)O$R^{21}$, —C(=O)$R^{21}$, —N($R^{24}$)$R^{21}$, —S(O)$_p$$R^{29}$, or —O$R^{29}$; and $Y^2$ is $Y^1$ or —OH, —SH, or —SO$_3$H;

(a) p is an integer from 0 to 2;

(b) $R^{24}$ is hydrogen; $C_1$–$C_8$ alkyl; $C_2$–$C_8$ alkenyl; a 3–8 atom heteroalkyl having one or two heteroatoms selected from O, S, or N; a 3–8 atom heteroalkenyl having one or two heteroatoms selected from O,S, or N; a 3–9 atom monocyclic or 7–17 atom polycyclic carbocycle; a 3–9 atom monocyclic or 7–17 atom polycyclic heterocycle; —SO$_3$H; —C(=O)$R^{25}$; or, when $R^{18}$ is —CH(N($R^{24}$)$R^{21}$)($R^{17}$), $R^{24}$ may comprise a moiety bonded to $R^{21}$ to form a 3–9 atom monocyclic or 7–17 atom polycyclic heterocycle; and wherein said heterocycle has one or more heteroatoms selected from O, S, or N;

(c) $R^{25}$ is $R^{17}$, NH($R^{17}$), N($R^{17}$)($R^{26}$), O($R^{26}$), or S($R^{26}$); where $R^{26}$ is $C_1$–$C_8$ alkyl, $C_2$–$C_8$ alkenyl, a 3–9 atom monocyclic or 7–17 atom polycyclic carbocycle, a 3–9 atom monocyclic or 7–17 atom polycyclic heterocycle, or when $R^{25}$ is N($R^{17}$)($R^{26}$), $R^{26}$ may be a moiety bonded to $R^{17}$ to form a 3–9 atom monocyclic or 7–17 atom polycyclic heterocycle; and wherein said heterocycle has one or more heteroatoms selected from O, S, or N;

(7) $R^{21}$ is $R^{29}$ or hydrogen; where $R^{29}$ is $C_1$–$C_8$ alkyl; $C_2$–$C_8$ alkenyl; aryl alkyl; heteroalkyl; a 3–8 atom heteroalkenyl having one or more heteroatoms selected from O, S, or N; a 3–8 atom heteroarylalkyl having one or more heteroatoms selected from O, S, or N; a 3–9 atom monocyclic or 7–17 atom polycyclic carbocycle; a 3–9 atom monocyclic or 7–17 atom polycyclic heterocycle; or, when Y is N($R^{24}$)$R^{21}$ and $R^{21}$ is $R^{29}$, $R^{21}$ and $R^{24}$ may together form a heterocycle including the nitrogen atom to which $R^{24}$ is bonded; wherein said heterocycle has one or more heteroatoms selected from O, S, or N; and wherein said arylalkyl is a $C_1$–$C_8$ alkyl substituted with an aryl group and wherein said heteroarylalkyl is a $C_1$–$C_8$ alkyl substituted with an aryl group substituted with a heteroatom selected from O, S, or N;

(D) $R^{11}$ is hydrogen, halogen, alkoxy, or $R^{27}$C(=O)NH—, where $R^{27}$ is hydrogen or alkyl;

(E) s is an integer from 0 to 2;

(F) $R^{37}$ is nil, alkyl, alkenyl, a carbocycle, or a heterocycle; and (G) $R^{38}$ is hydrogen, alkyl, or alkoxy.

(H) L is L', —$X^2_t$—$R^{39}$—L', or —$X^3_t$—$R^{39}$—L', where L' is Q', —$X^2$—Q", —$X^3$—Q", or —$X^4_t$—C(=$Y^3_u$)—Z—Q";

(1) t and u are, independently, 0 or 1;

(2) $R^{39}$ is $C_1$–$C_8$ alkyl, $C_2$–$C_8$ alkenyl, a heteroalkyl, 3–8 atom heteroalkenyl, a 3–9 atom monocyclic or 7–17 atom polycyclic carbocycle, or a 3–9 atom monocyclic or 7–17 atom polycyclic heterocycle wherein said heterocycle has one or more heteroatoms selected from O, S, or N;

(3) $X^2$ is oxygen, or S(O)$_v$, where v is an integer from 0 to 2;

(4) $X^3$ is nitrogen; N($R^{40}$); N$^+$($R^{41}$)($R^{42}$); or $R^{43}$—N($R^{41}$); and is linked to $R^{14}$ by a single or double bond;

(a) $R^{40}$ is $R^{8a}$; —OR$^{8a}$; or —C(=O)$R^{8a}$;

(b) $R^{41}$ and $R^{42}$ are, independently, hydrogen; $C_1$–$C_8$ alkyl; $C_2$–$C_8$ alkenyl; 3–9 atom monocyclic or 7–17 atom polycyclic carbocycles; wherein said heterocycle has one or more heteroatoms selected from O, S, or N heterocycles; or, if $R^6$ is $R^{16}$X, then $R^{41}$ and $R^{42}$ together with Q" may form a 3–9 atom monocyclic or 7–17 atom polycyclic heterocycle as $R^{16}$ wherein said heterocycle has one or more heteroatoms selected from O, S, or N;

(c) $R^{43}$ is N($R^{41}$), oxygen or sulfur;

(5) $X^4$ is oxygen, sulfur, NR$^{40}$, or $R^{43}$—NR$^{41}$;

(6) $Y^3$ is oxygen, sulfur, NR$^{40}$ or N$^+$($R^{41}$)($R^{42}$);

(7) $Y^4$ is oxygen or NR$^{41}$;

(8) Z is nil, oxygen, sulfur, nitrogen, NR$^{40}$, or N($R^{41}$)—$R^{43}$;

(9) Q' is said $R^6$ substituent of Q; and

(10) Q" is Q'; or together with $X^2$, $X^3$, Z or Z', is said $R^6$ substituent of Q;

and pharmaceutically-acceptable salts and biohydrolyzable esters thereof, and hydrates thereof.

2. A compound, according to claim 1, wherein $R^{10}$ is $R^{18}$—$(CH_2)_m$—C(=O)NH.

3. A compound, according to claim 2, wherein $R^{18}$ is $R^{17}$.

4. A compound, according to claim 2, wherein $R^{18}$ is —$Y^1$.

5. A compound, according to claim 2, wherein $R^{18}$ is —$CH(Y^2)(R^{17})$.

6. A compound, according to claim 1, wherein $R^{10}$ is $R^{17}$—C(=$CHR^{20}$)—C(=O)NH—.

7. A compound, according to claim 1, wherein $R^{10}$ is $R^{17}$—C(=NO—$R^{19}$)—C(=O)NH—.

8. A compound, according to claim 1, wherein $R^{11}$ is hydrogen or alkoxy.

9. A compound according to claim 8, wherein $R^{12}$ is —C($R^{8a}$)—.

10. A compound according to claim 1, wherein: $A^1$ is $C(R^7)$, $A^2$ is $C(R^2)$, and $A^3$ is $C(R^5)$; or $A^1$ is nitrogen, $A^2$ is $C(R^2)$, and $A^3$ is $C(R^5)$.

11. A compound according to claim 1, wherein $A^1$ is $C(R^7)$, $A^2$ is $C(R^2)$, and $A^3$ is $C(R^5)$.

12. A compound according to claim 11, wherein Q is a 6-fluoroquinolone moiety, a 8-halo-6-fluoroquinolone moiety, a pyridobenzoxazine moiety, a pyridobenthiazine moiety, a isothiazoloquinolinedione, or isoxazoloquinolinedione moiety.

13. A compound, according to claim 11, wherein $R^1$ is alkyl, aryl, cycloalkyl or alkylamino.

14. A compound, according to claim 13, wherein $R^1$ is ethyl, 2-fluoroethyl, 2-hydroxyethyl, t-butyl, 4-fluorophenyl, 2,4-difluorophenyl, methyl amino or cyclopropyl.

15. A compound, according to claim 13, wherein $R^2$ is hydrogen or halo.

16. A compound, according to claim 15, wherein $R^2$ is chlorine or fluorine.

17. A compound, according to claim 15, wherein $R^3$ is a nitrogen-containing heterocycle.

18. A compound, according to claim 17, wherein $R^3$ is piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, or 3,5-dimethylpiperazine.

19. A compound, according to claim 18, wherein $R^1$ is cyclopropyl, and $R^2$ is fluorine.

20. A compound, according to claim 19, wherein $R^3$ is piperazine.

21. A compound, according to claim 1, wherein L comprises a linking moiety selected from the group consisting of carbamate, dithiocarbamate, urea, thiourea, isouronium, isothiouronium, guanidine, carbonate, trithiocarbonate, reversed carbamate, xanthate, reversed isouronium, reversed dithiocarbamate, reversed isothiouronium, amine, imine, ammonium, heteroarylium, ether, thioether, ester, thioester, amide and hydrazide groups.

22. A compound, according to claim 21, wherein L is L', and L' is —$X^2$—Q", —$X^3$—Q", or $X^4_t$—C(=$Y^3_u$)—Z—Q".

23. A compound, according to claim 22, wherein Q" is said $R^6$ substituent of Q, or together with $X^2$, $X^3$, Z or Z', is said $R^6$ substituent of Q.

24. A compound, according to claim 16, wherein L' is $X^4_t$—C(=$Y^3_u$)—Z—Q".

25. A compound, according to claim 16, wherein t is 1, u is 1, and $X^4$ is is oxygen, sulfur or $NR^{40}$.

26. A compound, according to claim 22, wherein said linking moiety is selected from the group consisting of carbamate, dithiocarbamate, urea, thiourea, isothiouronium, amine, ammonium, and heteroarylium groups.

27. A compound, according to claim 26, wherein said linking moiety is a carbamate or dithiocarbamate group.

28. A compound according to claim 1, wherein L is other than an ester.

29. A compound according to claim 28 wherein L is chosen from the group consisting of carbamate, dithiocarbamate, Urea, thiourea, isouronium, iso thiouronium, guanidinium, carbonate, trithiocarbonare, reversed carbamate, Xanthate, Reversed dithiocarbamate, reversed isothiouriom, amine, imine, heteroarylium, ether, thioether and hydrazide.

30. A compound according to claim 1 wherein L is an ester.

* * * * *